(12) United States Patent
Lecloux et al.

(10) Patent No.: US 8,497,495 B2
(45) Date of Patent: Jul. 30, 2013

(54) ELECTROACTIVE MATERIALS

(75) Inventors: Daniel David Lecloux, Wilmington, DE (US); Adam Fennimore, Wilmington, DE (US); Weiying Gao, Landenberg, PA (US); Nora Sabina Radu, Landenberg, PA (US); Michael Henry Howard, Jr., Montchanin, DE (US); Gary A. Johansson, Hockessin, DE (US); Kalindi Dogra, Wilmington, DE (US); Eric Maurice Smith, Hockessin, DE (US); Kyung-Ho Park, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 698 days.

(21) Appl. No.: 12/643,486

(22) Filed: Dec. 21, 2009

(65) Prior Publication Data
US 2010/0252819 A1   Oct. 7, 2010

Related U.S. Application Data

(60) Provisional application No. 61/166,400, filed on Apr. 3, 2009.

(51) Int. Cl.
*H01L 51/54* (2006.01)
(52) U.S. Cl.
USPC ................................ 257/40; 257/E51.027
(58) Field of Classification Search
USPC ........................................ 257/40, E51.027
See application file for complete search history.

(56) References Cited

U.S. PATENT DOCUMENTS

| 3,282,875 | A | 11/1966 | Connolly et al. |
|---|---|---|---|
| 3,720,515 | A | 3/1973 | Stanley |
| 3,849,458 | A | 11/1974 | Dinh |
| 4,053,311 | A | 10/1977 | Limburg et al. |
| 4,358,545 | A | 11/1982 | Ezzell et al. |
| 4,940,525 | A | 7/1990 | Ezzell |
| 5,247,190 | A | 9/1993 | Friend et al. |
| 5,254,633 | A | 10/1993 | Han |
| 5,378,519 | A | 1/1995 | Kikuchi et al. |
| 5,408,109 | A | 4/1995 | Heeger et al. |
| 5,707,747 | A | 1/1998 | Tomiyama et al. |
| 5,911,918 | A | 6/1999 | Shacklette et al. |
| 5,929,194 | A | 7/1999 | Woo et al. |
| 5,936,259 | A | 8/1999 | Katz et al. |
| 5,962,631 | A | 10/1999 | Woo et al. |
| 6,150,426 | A | 11/2000 | Curtin et al. |
| 6,259,202 | B1 | 7/2001 | Sturm et al. |

(Continued)

FOREIGN PATENT DOCUMENTS

| DE | 102005058557 A1 | 6/2007 |
|---|---|---|
| EP | 443861 A2 | 7/1995 |

(Continued)

OTHER PUBLICATIONS

CRC Handbook of Chemistry and Physics, 81$^{st}$ Edition (2000-2001) (Book Not Included).

(Continued)

*Primary Examiner* — Calvin Lee
*Assistant Examiner* — Monica D Harrison

(57) ABSTRACT

A compound having at least two diarylamino moieties and at least 10% deuteration.

24 Claims, 2 Drawing Sheets

U.S. PATENT DOCUMENTS

| | | |
|---|---|---|
| 6,303,238 B1 | 10/2001 | Thompson et al. |
| 6,579,630 B2 | 6/2003 | Li et al. |
| 6,670,645 B2 | 12/2003 | Grushin et al. |
| 6,677,060 B2 | 1/2004 | Li et al. |
| 6,686,067 B2 | 2/2004 | Li et al. |
| 6,852,429 B1 | 2/2005 | Li et al. |
| 6,872,475 B2 | 3/2005 | Chen et al. |
| 6,875,524 B2 | 4/2005 | Hatwar et al. |
| 6,902,833 B2 | 6/2005 | Thompson et al. |
| 6,953,705 B2 | 10/2005 | Prakash |
| 7,023,013 B2 | 4/2006 | Ricks et al. |
| 7,075,102 B2 | 7/2006 | Grushin et al. |
| 7,125,952 B2 | 10/2006 | O'Dell et al. |
| 7,173,131 B2 | 2/2007 | Saitoh et al. |
| 7,189,989 B2 | 3/2007 | Ise |
| 7,211,202 B2 | 5/2007 | Korzhenko et al. |
| 7,235,420 B2 | 6/2007 | Prakash et al. |
| 7,351,358 B2 | 4/2008 | Hsu et al. |
| 7,358,409 B2 | 4/2008 | Saitoh et al. |
| 7,362,796 B2 | 4/2008 | Shigeno |
| 7,365,230 B2 | 4/2008 | Herron et al. |
| 7,375,250 B2 | 5/2008 | Saitoh et al. |
| 7,390,438 B2 | 6/2008 | Hsu et al. |
| 7,402,681 B2 | 7/2008 | Ong et al. |
| 7,431,866 B2 | 10/2008 | Hsu et al. |
| 7,456,424 B2 | 11/2008 | Wu et al. |
| 7,462,298 B2 | 12/2008 | Hsu et al. |
| 7,491,450 B2 | 2/2009 | Okinaka et al. |
| 7,528,542 B2 | 5/2009 | Kawamura et al. |
| 7,540,978 B2 | 6/2009 | Pfeiffer et al. |
| 7,586,006 B2 | 9/2009 | Funahashi |
| 7,642,380 B2 | 1/2010 | Funahashi |
| 7,651,786 B2 | 1/2010 | Matsuura et al. |
| 7,651,788 B2 | 1/2010 | Seo et al. |
| 7,709,104 B2 | 5/2010 | Saitoh et al. |
| 7,722,785 B2 | 5/2010 | Hsu et al. |
| 7,745,017 B2 | 6/2010 | Nakamura et al. |
| 7,887,933 B2 | 2/2011 | Kathirgamanathan et al. |
| 8,026,665 B2 | 9/2011 | Kim et al. |
| 8,063,399 B2 | 11/2011 | Johansson et al. |
| 8,343,381 B1 | 1/2013 | Chesterfield |
| 2001/0026878 A1 | 10/2001 | Woo et al. |
| 2001/0053462 A1 | 12/2001 | Mishima |
| 2002/0048687 A1 | 4/2002 | Hosokawa et al. |
| 2002/0076576 A1* | 6/2002 | Li et al. .......... 428/690 |
| 2002/0155319 A1 | 10/2002 | Kawamura et al. |
| 2003/0072966 A1 | 4/2003 | Hosokawa et al. |
| 2003/0118866 A1 | 6/2003 | Oh et al. |
| 2003/0134140 A1 | 7/2003 | Li |
| 2003/0138657 A1 | 7/2003 | Li |
| 2003/0168970 A1 | 9/2003 | Tominaga et al. |
| 2003/0224205 A1 | 12/2003 | Li et al. |
| 2003/0227001 A1 | 12/2003 | Li et al. |
| 2004/0004433 A1 | 1/2004 | Lamansky et al. |
| 2004/0038459 A1 | 2/2004 | Brown et al. |
| 2004/0082250 A1 | 4/2004 | Haoto |
| 2004/0094768 A1 | 5/2004 | Yu et al. |
| 2004/0102577 A1 | 5/2004 | Hsu et al. |
| 2004/0106003 A1 | 6/2004 | Chen et al. |
| 2004/0106004 A1 | 6/2004 | Li |
| 2004/0121184 A1 | 6/2004 | Thompson et al. |
| 2004/0127637 A1 | 7/2004 | Hsu et al. |
| 2004/0189190 A1 | 9/2004 | Suzuri et al. |
| 2004/0209118 A1 | 10/2004 | Seo et al. |
| 2004/0263067 A1 | 12/2004 | Saitoh et al. |
| 2005/0031898 A1 | 2/2005 | Li et al. |
| 2005/0035335 A1 | 2/2005 | Han et al. |
| 2005/0063638 A1 | 3/2005 | Alger et al. |
| 2005/0064233 A1 | 3/2005 | Matsuura et al. |
| 2005/0073249 A1 | 4/2005 | Morii et al. |
| 2005/0158577 A1 | 7/2005 | Ishibashi et al. |
| 2005/0184287 A1 | 8/2005 | Herron et al. |
| 2005/0186106 A1 | 8/2005 | Li et al. |
| 2005/0187411 A1 | 8/2005 | Herron et al. |
| 2005/0191776 A1 | 9/2005 | Lamansky et al. |
| 2005/0205860 A1 | 9/2005 | Hsu et al. |
| 2005/0244670 A1 | 11/2005 | Saitoh et al. |
| 2005/0245752 A1 | 11/2005 | Conley et al. |
| 2005/0280008 A1 | 12/2005 | Ricks et al. |
| 2006/0033421 A1 | 2/2006 | Matsuura et al. |
| 2006/0043858 A1 | 3/2006 | Ikeda et al. |
| 2006/0052641 A1 | 3/2006 | Funahashi |
| 2006/0076557 A1 | 4/2006 | Waller et al. |
| 2006/0103298 A1 | 5/2006 | Lee |
| 2006/0113528 A1 | 6/2006 | Okinaka et al. |
| 2006/0115676 A1 | 6/2006 | Igawa et al. |
| 2006/0115678 A1 | 6/2006 | Saitoh et al. |
| 2006/0121312 A1 | 6/2006 | Yamada et al. |
| 2006/0127698 A1 | 6/2006 | Tokailin et al. |
| 2006/0128969 A1 | 6/2006 | Li et al. |
| 2006/0134459 A1 | 6/2006 | Huo |
| 2006/0152146 A1 | 7/2006 | Funahashi |
| 2006/0154107 A1 | 7/2006 | Kubota et al. |
| 2006/0158102 A1 | 7/2006 | Kawamura et al. |
| 2006/0159838 A1 | 7/2006 | Kowalski et al. |
| 2006/0194074 A1 | 8/2006 | Funahashi |
| 2006/0210830 A1 | 9/2006 | Funahashi |
| 2006/0216411 A1 | 9/2006 | Steudel et al. |
| 2006/0217572 A1 | 9/2006 | Kawamura et al. |
| 2006/0251925 A1 | 11/2006 | Hosokawa et al. |
| 2006/0267488 A1 | 11/2006 | Saitoh et al. |
| 2006/0284140 A1 | 12/2006 | Breuning et al. |
| 2007/0031588 A1 | 2/2007 | Nakayama |
| 2007/0031701 A1 | 2/2007 | Nakashima et al. |
| 2007/0032632 A1 | 2/2007 | Tsukioka et al. |
| 2007/0063638 A1 | 3/2007 | Tokairin et al. |
| 2007/0066755 A1 | 3/2007 | Hsu et al. |
| 2007/0079927 A1 | 4/2007 | Lamansky et al. |
| 2007/0096082 A1 | 5/2007 | Gaynor et al. |
| 2007/0114917 A1 | 5/2007 | Funahashi et al. |
| 2007/0134511 A1 | 6/2007 | Kawamura et al. |
| 2007/0155991 A1 | 7/2007 | Funahashi |
| 2007/0181874 A1 | 8/2007 | Prakash et al. |
| 2007/0189190 A1 | 8/2007 | Feng et al. |
| 2007/0205409 A1 | 9/2007 | Lecloux et al. |
| 2007/0215864 A1 | 9/2007 | Luebben et al. |
| 2007/0228364 A1 | 10/2007 | Radu et al. |
| 2007/0236137 A1 | 10/2007 | Funahashi |
| 2007/0247063 A1 | 10/2007 | Murase et al. |
| 2007/0252511 A1 | 11/2007 | Funahashi |
| 2007/0255076 A1 | 11/2007 | Ito et al. |
| 2007/0285009 A1 | 12/2007 | Kubota |
| 2007/0292713 A9 | 12/2007 | Dobbs et al. |
| 2007/0298530 A1 | 12/2007 | Feehery |
| 2008/0023676 A1 | 1/2008 | Hsu |
| 2008/0049413 A1 | 2/2008 | Jinde et al. |
| 2008/0067473 A1 | 3/2008 | Walker et al. |
| 2008/0067924 A1 | 3/2008 | Prakash et al. |
| 2008/0086012 A1 | 4/2008 | Egawa et al. |
| 2008/0097076 A1 | 4/2008 | Radu et al. |
| 2008/0102312 A1 | 5/2008 | Parham et al. |
| 2008/0114178 A1 | 5/2008 | Kawakami et al. |
| 2008/0138655 A1 | 6/2008 | Lecloux et al. |
| 2008/0166566 A1 | 7/2008 | Prakash |
| 2008/0191614 A1 | 8/2008 | Kim et al. |
| 2008/0233433 A1 | 9/2008 | Igarashi et al. |
| 2008/0286487 A1 | 11/2008 | Lang et al. |
| 2008/0286566 A1 | 11/2008 | Prakash |
| 2008/0286605 A1 | 11/2008 | Takeda |
| 2008/0297037 A1 | 12/2008 | Vestweber et al. |
| 2008/0303425 A1 | 12/2008 | Rostovtsev et al. |
| 2008/0303427 A1 | 12/2008 | Johansson et al. |
| 2008/0303428 A1 | 12/2008 | Rostovtsev et al. |
| 2008/0315754 A1 | 12/2008 | Kawamura et al. |
| 2009/0051281 A1 | 2/2009 | Inoue |
| 2009/0058279 A1 | 3/2009 | Takeda |
| 2009/0079334 A1 | 3/2009 | Kim et al. |
| 2009/0114909 A1 | 5/2009 | Li et al. |
| 2009/0134781 A1 | 5/2009 | Jang et al. |
| 2009/0184635 A1 | 7/2009 | Pan et al. |
| 2009/0206748 A1 | 8/2009 | Moriwaki et al. |
| 2009/0295274 A1 | 12/2009 | Hwang et al. |
| 2009/0302742 A1 | 12/2009 | Komori et al. |
| 2010/0108989 A1 | 5/2010 | Büsing et al. |
| 2010/0148161 A1 | 6/2010 | Kai et al. |
| 2010/0148162 A1 | 6/2010 | Komori et al. |
| 2010/0187505 A1 | 7/2010 | Stoessel et al. |

| | | | |
|---|---|---|---|
| 2010/0187506 A1 | 7/2010 | Park et al. | |
| 2010/0187507 A1 | 7/2010 | Park et al. | |
| 2010/0187977 A1 | 7/2010 | Kai et al. | |
| 2010/0187983 A1* | 7/2010 | Herron et al. | 313/504 |
| 2010/0213825 A1 | 8/2010 | Park et al. | |
| 2010/0314644 A1 | 12/2010 | Nishimura et al. | |
| 2011/0037062 A1 | 2/2011 | Fukumatsu et al. | |
| 2011/0095269 A1 | 4/2011 | Zhang et al. | |
| 2011/0095273 A1 | 4/2011 | Meng et al. | |
| 2011/0121269 A1 | 5/2011 | Lecloux et al. | |
| 2011/0147718 A1 | 6/2011 | Howard, Jr. et al. | |

FOREIGN PATENT DOCUMENTS

| | | | |
|---|---|---|---|
| EP | 681019 A2 | 9/1999 | |
| EP | 1061112 A1 | 12/2000 | |
| EP | 765106 A2 | 11/2002 | |
| EP | 1277824 A1 | 1/2003 | |
| EP | 1317005 A2 | 6/2003 | |
| EP | 1437395 A2 | 7/2004 | |
| EP | 1491609 A2 | 12/2004 | |
| EP | 1491610 A2 | 12/2004 | |
| EP | 1541657 A1 | 6/2005 | |
| EP | 1561794 A1 | 8/2005 | |
| EP | 1604974 A1 | 12/2005 | |
| EP | 1612202 A1 | 1/2006 | |
| EP | 1624500 A1 | 2/2006 | |
| EP | 1672713 A1 | 6/2006 | |
| EP | 1718124 A1 | 11/2006 | |
| EP | 1737277 A1 | 12/2006 | |
| EP | 1933603 A1 | 6/2008 | |
| EP | 1956022 A1 | 8/2008 | |
| EP | 1995292 A1 | 11/2008 | |
| EP | 2080762 A1 | 7/2009 | |
| EP | 2085450 A1 | 8/2009 | |
| EP | 2093271 A1 | 8/2009 | |
| EP | 2067766 A1 | 10/2009 | |
| EP | 2067767 A1 | 10/2009 | |
| EP | 2189508 A3 | 3/2011 | |
| JP | 04175395 A | 6/1992 | |
| JP | 07249490 A | 9/1995 | |
| JP | 08053397 A | 2/1996 | |
| JP | 08167479 A | 6/1996 | |
| JP | 10251633 A | 9/1998 | |
| JP | 11224779 A | 8/1999 | |
| JP | 11338172 A | 12/1999 | |
| JP | 2000068073 A | 3/2000 | |
| JP | 2000186066 A | 7/2000 | |
| JP | 2001039933 A | 2/2001 | |
| JP | 2001226331 A | 8/2001 | |
| JP | 2002506481 A | 2/2002 | |
| JP | 2002293888 A | 10/2002 | |
| JP | 2003026641 A | 1/2003 | |
| JP | 2003238501 A | 8/2003 | |
| JP | 2004-10550 A | 1/2004 | |
| JP | 2004014187 A | 1/2004 | |
| JP | 2004107292 A | 4/2004 | |
| JP | 2006016384 A | 1/2006 | |
| JP | 2006052323 A | 2/2006 | |
| JP | 2006-151844 A | 6/2006 | |
| JP | 2006140235 A | 6/2006 | |
| JP | 2006176493 A | 7/2006 | |
| JP | 2006-219392 A | 8/2006 | |
| JP | 2006328037 A | 12/2006 | |
| JP | 2007-186449 A | 7/2007 | |
| JP | 2007182432 A | 7/2007 | |
| JP | 2007186449 A | 7/2007 | |
| JP | 2007208165 A | 8/2007 | |
| JP | 2009161470 A | 7/2009 | |
| JP | 2009246354 A | 10/2009 | |
| KR | 1020040079803 A | 9/2004 | |
| KR | 1020050073233 A | 7/2005 | |
| KR | 100702763 B1 | 4/2007 | |
| KR | 1020070091293 A | 9/2007 | |
| KR | 100765728 B1 | 10/2007 | |
| KR | 10-2009-0046731 A | 5/2009 | |
| KR | 10-2009-0086015 A | 8/2009 | |
| KR | 10-2009-0086920 A | 8/2009 | |
| KR | 10-2009-0093897 A | 9/2009 | |
| WO | 9954385 A1 | 10/1999 | |
| WO | 0053565 A1 | 9/2000 | |
| WO | 0070655 A2 | 11/2000 | |
| WO | 0141512 A1 | 6/2001 | |
| WO | 02051958 A1 | 7/2002 | |
| WO | 03008424 A1 | 1/2003 | |
| WO | WO03/008424 A1 | 1/2003 | |
| WO | 03040257 A1 | 5/2003 | |
| WO | WO03/040257 A1 | 5/2003 | |
| WO | 03063555 A1 | 7/2003 | |
| WO | WO03/063555 A1 | 7/2003 | |
| WO | 03091688 A2 | 11/2003 | |
| WO | WO03/091688 A2 | 11/2003 | |
| WO | 2004016710 A1 | 2/2004 | |
| WO | WO2004/016710 A1 | 2/2004 | |
| WO | 2004018587 A1 | 3/2004 | |
| WO | 2004041901 A1 | 5/2004 | |
| WO | 2004058913 A1 | 7/2004 | |
| WO | 2005000787 A1 | 1/2005 | |
| WO | 2005049546 A1 | 6/2005 | |
| WO | 2005049548 A1 | 6/2005 | |
| WO | 2005049689 A2 | 6/2005 | |
| WO | WO2005/052027 A1 | 6/2005 | |
| WO | 2005115950 A1 | 12/2005 | |
| WO | 2006001333 A1 | 1/2006 | |
| WO | 2006025273 A1 | 3/2006 | |
| WO | 2006057326 A1 | 6/2006 | |
| WO | 2006063852 A1 | 6/2006 | |
| WO | 2006076146 A2 | 7/2006 | |
| WO | 2006090772 A1 | 8/2006 | |
| WO | 2006112582 A1 | 10/2006 | |
| WO | 2006121237 A1 | 11/2006 | |
| WO | 2006137210 A1 | 12/2006 | |
| WO | 2007004364 A1 | 1/2007 | |
| WO | 2007021117 A1 | 2/2007 | |
| WO | 2007065678 A1 | 6/2007 | |
| WO | 2007076146 A2 | 7/2007 | |
| WO | 2007108457 A1 | 9/2007 | |
| WO | WO2007-100096 A1 | 9/2007 | |
| WO | WO2007-105917 A1 | 9/2007 | |
| WO | WO2007/108666 A1 | 9/2007 | |
| WO | 2007129702 A1 | 11/2007 | |
| WO | 2008011953 A1 | 1/2008 | |
| WO | WO2008/024378 A2 | 2/2008 | |
| WO | WO2008/024379 A2 | 2/2008 | |
| WO | 2008078114 A1 | 7/2008 | |
| WO | WO2008-149968 A1 | 12/2008 | |
| WO | 2009018009 A1 | 2/2009 | |
| WO | WO2009/028902 A2 | 3/2009 | |
| WO | WO2009-055628 A1 | 4/2009 | |
| WO | WO2009/067419 A1 | 5/2009 | |
| WO | 2009069790 A1 | 6/2009 | |
| WO | 2010065494 A2 | 6/2010 | |
| WO | 2010071362 A2 | 6/2010 | |
| WO | 2010075421 A2 | 7/2010 | |
| WO | 2010099534 A2 | 9/2010 | |
| WO | 2010135403 A2 | 11/2010 | |
| WO | 2011053334 A1 | 5/2011 | |

OTHER PUBLICATIONS

"Flexible light-emitting diodes made from soluble conducting polymer" Nature, vol. 357, pp. 477 479 (Jun. 11, 1992).

Kirk-Othmer Encyclopedia of Chemical Technology, Fourth Edition, vol. 18, pp. 837-860, 1996 Y. Wang.

Markus, John, Electronics and Nucleonics dictionary, 470 and 476 (McGraw-Hill 1966).

International Search Report, Korean Intellectual Property Office, Daejeon, Republic of Korea, PCT/US2009/068921, PCT Counterpart of the Present U.S. Appl. No. 12/643,486, Hyun Shik Oh, Authorized Officer, Aug. 5, 2010.

International Search Report, Korean Intellectual Property Office, Daejeon, Republic of Korea, in PCT/2009/068918, PCT copending U.S. Appl. No. 12/643,403, Jun Gyu Kim, Authorized Officer, Jul. 26, 2010.

International Search Report, Korean Intellectual Property Office, Daejeon, Republic of Korea, in PCT/2010/025764, PCT copending U.S. Appl. No. 12/714,880, Hyun Shik Oh, Authorized Officer, Sep. 27, 2010.

International Search Report, Korean Intellectual Property Office, Daejeon, Republic of Korea, in PCT/2009/068922, PCT copending U.S. Appl. No. 12/643,567, Hyun Shik Oh, Authorized Officer, Oct. 20, 2010.

International Search Report, Korean Intellectual Property Office, Daejeon, Republic of Korea, in PCT/2009/068928, PCT copending U.S. Appl. No. 12/643,511, Hyun Shik Oh, Authorized Officer, Aug. 17, 2010.

International Search Report, Korean Intellectual Property Office, Daejeon, Republic of Korea, in PCT/2010/035356, PCT copending U.S. Appl. No. 12/782,781, Hyun Shik Oh, Authorized Officer, Dec. 24, 2010.

International Search Report, Korean Intellectual Property Office, Daejeon, Republic of Korea, in PCT/2009/068945, PCT copending U.S. Appl. No. 12/643,420, Hyun Shik Oh, Authorized Officer, Sep. 27, 2010.

International Search Report, Korean Intellectual Property Office, Daejeon, Republic of Korea, in PCT/2009/068950, PCT copending U.S. Appl. No. 12/643,449, Hyun Shik Oh, Authorized Officer, Jan. 3, 2011.

International Search Report, Korean Intellectual Property Office, Daejeon, Republic of Korea, in PCT/2009/068956, PCT copending U.S. Appl. No. 12/643,487, Hyun Shik Oh, Authorized Officer, Sep. 6, 2010.

International Search Report, Korean Intellectual Property Office, Daejeon, Republic of Korea, in PCT/2009/069255, PCT copending U.S. Appl. No. 12/643,459, Hyun Shik Oh, Authorized Officer, Aug. 13, 2010.

International Search Report, Korean Intellectual Property Office, Daejeon, Republic of Korea, in PCT/2009/068976, PCT copending U.S. Appl. No. 12/643,515, Bum Soo Kim, Authorized Officer, Jan. 28, 2011.

Beckmann et al., "Methyl Reorientation in Solid 3-ethychrysene and 3-isopropylesene; Solid State Nuclear Magnetic Resonance," 1998; vol. 12; pp. 251-256.

Boix et al., "Efficient H-D Exchange of Aromatic Compounds in Near-Critical D2O Catalyzed by a Polymer-Supported Sulphonic Acid," Tetrahedron Letters, 1999, vol. 40, pp. 4433-4436.

Borello et al., "Photodetectors," Kirk-Othmer Encyclopedia of Chemical Technology, Fourth Edition, 1999, vol. 18, pp. 1537-1538.

Braun et al., "Visible Light Emission from Semiconducting Polymer Diodes," Applied Physics Letters, 1991, vol. 58 (18), pp. 1982-1984.

Carey et al., Structure and Mechanisms; Advanced Organic Chemistry, Part A, 5th Edition, pp. 142-145.

Chen et al., "Efficient, Blue Light-Emnitting Diodes Using Cross-Linked Layers of Polymeric Arylamine and Fluorene," Synthetic Metals, 1999, vol. 107, pp. 129-138.

Chu et al., "Highly Efficient and Stable Inverted Bottom-Emission Organic Light Emitting Devices," Applied Physics Letters, 2006, vol. 89, 053503.

Colon et al., "High Molecular Weight Aromatic Polymers by Nickel Coupling of Aryl Polychlorides," Journal of Polymer Science, Part A, Polymer Chemistry Edition, 1990, vol. 28, pp. 367-383.

Danel et al., "Blue-Emitting Anthracenes with End-Capping Diarylamines," Chem. Mater., 2002, vol. 14, pp. 3860-3865.

Eaton et al., "Dihedral Angle of Biphenyl in Solution and the Molecular Force Field," Journal of the Chemical Society: Faraday Transactions 2, 1973, vol. 60, pp. 1601-1608.

Esaki et al., "Efficient H/D Exchange Reactions of Alkyl-Substituted Benzene Derivatives by Means of the Pd/C—H—D2O System," Chemistry: A European Journal, 2007, vol. 13, pp. 4052-4063.

Guo et al., "Aromatic H/D Exchange Reaction Catalyzed by Groups 5 and 6 Metal Chlorides," Chinese Journal of Chemistry, 2005, vol. 23, pp. 341-344.

He et al., "A Hole-Transporting Material with Controllable Morphology Containing Binaphtyl and Triphenylamine Chromophores," Advanced Functional Materials, vol. 16, No. 10, pp. 1343-1348.

He et al., "High-efficiency Organic Polymer Light-emitting Heterostructure Devices on Flexible Plastic Substrates," Applied Physics Letters, 2000, vol. 76, No. 6, pp. 661-663.

Ishiyama et al., "Palladium(0)-Catalyzed Cross-Coupling Reaction of Alkoxydiboron with Haloarenes: A Direct Procedure for Arylboronic Esters," Journal of Organic Chemistry, 1995, vol. 60, pp. 7508-7510.

Kim et al., "Synthesis and Electroluminescent Properties of Highly Efficient Anthracene Derivatives with Bulky Side Groups," Organic Electronics, 2009, vol. 10, No. 5, pp. 822-833.

Klaerner et al., "Cross-Linkable Polymers Based on Dialkylfluorenes," Chemistry of Materials, 1999, 11, pp. 1800-1805.

Kodomari et al., "Selective Halogenation of Aromatic Hydrocarbons," Journal of Organic Chemistry,1988, vol. 53, p. 2093.

Kumada, "Nickel and Palladium Complex Catalyzed Cross-Coupling Reactions of Organometallic Reagents with Organic Halides," Pure & Applied Chemistry, 1980, vol. 52, pp. 669-679.

Lee et al., "A Thermally Stable Hole Injection Material for Use in Organic Light-Emitting Diodes," Thin Solid Films, 2007, vol. 515, pp. 7726-7731.

Leznoff et al,, "Photocyclization of Aryl Polyenes. V. Photochemical Synthesis of Substituted Chrysenes," Canadian Journal of Chemistry, 1972, vol. 50, pp. 528-533.

Mueller et al., "Synthesis and Characterization of Soluble Oligo(9,10-anthrylene)s," Chemische Berichte, 1994, 127, pp. 437-444.

Murata et al., "Novel Palladium(0)-Catalyzed Coupling Reaction of Dialkoxyborane with Aryl Halides: A Convenient Synthetic Route to Arylboronates," Journal of Organic Chemistry, 1997, vol. 62, pp. 6458-6459.

Murata et al., "Palladium-Catalyzed Borylation of Aryl Halides or Triflates with Dialkoxyborane: A Novel and Facile Synthetic Route to Aryboronates," Journal of Organic Chemistry, 2000, vol. 65, No. 1,pp. 164-168.

Negishi et al; III.2.15 Palladium Catalyzed Conjugate Substitution; Handbook of Organopalladium Chemistry for Organic Synthesis, 2000, vol. 1, pp. 767-789.

Negishi, "Palladium- or Nickel-Catalyzed Cross Coupling. A New Selective Method for Carbon-Carbon Bond Formation," Accounts of Chemical Research, 1982, vol. 15, pp. 340-348.

Noji et al., "A New Catalytic System for Aerobic Oxidative Coupling of 2-Naphthol Derivatives by the Use of CuCl-Amine Complex: A Practical Synthesis of Binaphthol Derivatives," Tetrahedron Letters, 1994, vol. 35, No. 43, pp. 7983-7984.

Sajiki et al., "Efficient C-H/C-D Exhange Reaction on the Alkyl Side Chain of Aromatic Compounds Using Heterogenous Pd/C in D2O," Organic Letters, 2004, vol. 6, No. 9, pp. 1485-1487.

Stille, "The Palladium-Catalyzed Cross-Coupling Reactions of Organotin Reagents with Organic Electrophiles," Angew. Chem. Int. Ed. Engl., 1986, vol. 25, pp. 508-524.

Tong et al., "Enhancement of OLED Efficiencies and High-Voltage Stabilities of Light-Emitting Materials by Deuteration," Journal of Physical Chemistry, 2007, vol. 111, pp. 3490-3494.

Watts et al., "A Novel Deuterium Effect of Dual Charge-Transfer and Ligand-Field Emission of the cis-Dichlorobis (2,2'-bipyridine)iridium(III) Ion," Journal of the American Chemical Society, 1979, vol. 101(10), pp. 2742-2743.

Weine et al., "Reactions of an O-Quinone Monoimide with Anthracenes, Phencyclone, and 1,3-Diphenylisobenzofuran," Journal of Organic Chemistry, 1989, vol. 54, pp. 5926-5930.

Wellmann et al., "High Efficiency p-i-n Organic Light-Emitting Diodes with Long Lifetime," Journal of the SID, 2005, vol. 13/5, pp. 393-397393.

Yamada et al., "Synthesis of 2,9-Dichloro-1,10-phenanthroline from N,N'-Annelated Phenanthrolinediones," Bulletin of the Chemical Society of Japan, 1990, vol. 63, No. 9, pp. 2710-2712.

Yamamoto et al., "Electrically conducting and thermally stable pi-conjugated poly(arylene)s prepared by organometallic process," Progress in Polymer Science, 1992, vol. 17, pp. 1153-1205.

Yan et al., "Synthesis and Nonlinear Optical Properties of Novel Multi-Branched Two-Photon Polymerization Initiators," Journal of Material Chemistry, 2004, vol. 14, pp. 2295-3000.

Zhao et al., "Solid-State Dye-Sensitized Photovoltaic Device with Newly Designed Small Organic Molecule as Hole-Conductor," Chemical Physical Letters, 2007, vol. 445, pp. 259-264.

Zhu et al., "An Improved Preparation of Arylboronates: Application in One-Pot Suzuki Biaryl Synthesis," Journal of Organic Chemistry, 2003, vol. 68, pp. 3729-3732.

Zhu et al., "Effect of ITO Carrier Concentration on the Performance of Light-Emitting Diodes," 2000; Material Research Society; Chem Abstract 134: 122994.

PCT International Search Report for Application No. PCT/US2007/018530, counterpart to U.S. Appl. No. 11/843,029; C. Meiners, Authorized Officer; EPO; Feb. 7, 2008.

PCT International Search Report for Application No. PCT/US2007/018531, counterpart to U.S. Appl. No. 11/843,041; D. Marsitzky, Authorized Officer; Feb. 26, 2008.

PCT International Search Report for Application No. PCT/US2008/065191, counterpart to U.S. Appl. No. 12/129,729; Wolfgang Fitz, Authorized Officer; Sep. 4, 2008.

PCT International Search Report for Application No. PCT/US2008/083844, counterpart to U.S. Appl. No. 12/272,210; S. Saldamli, Authorized Officer; Jan. 28, 2009.

"Color." (Definition) Web. Sep. 27, 2011, <http://hyperphysics.phy-astr.gsu/Hbase/vision/secpl>.

Appleby et al., Polymeric Perfluoro Bis-Sulfanomides as Possible Fuel Cell Electrolytes, J. Electrochem. Soc., 1993, vol. 140, pp. 109-111.

Chu et al., "Comparitive Study of Single and Multiemissive Layers in Inverted White Organic Light-Emitting Devices," Applied Physics Letters, 2006, vol. 89, No. 11, pp. 113502.

Constantini et al., "Infrared Spectroscopic Study of Polaron Formation in Electrochemically Synthesized Poly(3-alkylpyrroles)," Phys. Chem. Chem. Phys., 2003 vol. 5, pp. 749-757.

Desmarteau, "Novel Perfluorinated Ionomers and Ionenes," Journal of Fluorine Chemistry, 1995, vol. 72, pp. 203-208.

Feiring et al., "Aromatic Monomers with Pendant Fluoroalkylsulfonate and Sulfonimide Groups," Journal of Fluorine Chemistry, 2000, vol. 105, pp. 129-135.

Feiring et al., "Novel Aromatic Polymers with Pendant Lithium Periluoroalkylsulfonate or Sulfinimide Groups," Macromolecules, 2000, vol. 33, pp. 9262-9271.

Hartwig, "Carbon-Heteroatom Bond Formation Catalyzed by Organometallic Complexes," Nature, 2008 vol. 455, No. 18, pp. 314-322.

Hartwig, "Discovery and Understanding of Transition-Metal-Catalyzed Aromatic Substitution Reactions," Syn Lett., 2006, No. 9, pp. 1283-1294.

Lee et al., "Poly(thieno(3,4-b)thiophene) A New Stable Low Band Gap Conducting Polymer," Macromolecules, 2001, vol. 34, pp. 5746-5747.

Maeda et al., "Alkynylpyrenes as Improved Pyrene-Based Biomolecular Probes with the Advantages of High Fluorescence Quantum Yields and Long Absorption/Emission Wavelengths," Chemisty—A European Journal, 2006, vol. 12(3), pp. 824-831.

March, Aromatization of Six-Membered Rings, Advanced Organic Chemistry, Wiley-Interscience (1992), 4th Ed., pp. 1162-1164.

Minabe et al., "Electrophilic Substitution of Monosubstituted Pyrenes," Bulletin of the Chemical Society of Japan (1994), 67(1), pp. 172-179.

Norman et al., "The Reactions of Pyrene with Free Radicals and with Sodium," Journal of the Chemical Society, 1958, pp. 175-179.

Park et al., "Ab Inition Study of Pyrenes for Blue Organic Light-Emitting Diodes," Molecular Crystals and Liquid Crystals, 2006, vol. 444, pp. 177-184.

Sheldon et al., "The Mechanism of the Collision-induced Loss of Methane from the Trimethylsilyl Negative Ion," Perkin Transaction II: Organic and Bio-Organic Chemistry, Journal of the Chemical Society (1988), (7), pp. 1263-1268.

Sotzing et al., "Poly(thieno(3,4-b)thiophene): A p- and n-Dopable Polythiophene Exhibiting High Optical Transparency in the Semiconducting State," Macromolecules, 2002, vol. 35, pp. 7281-7286.

Sze, S.M., Physics of Semiconductor Devices, 2nd Edition,1981, John Wiley & Sons, p. 492.

Tokito et al., "Highly Efficient Blue-Green Emission from Organic Light-Emitting Diodes Using Dibenzochrysene Derivatives," Applied Physics Letters, 2000, vol. 77, No. 2, pp. 160-162.

Wang et al., "Novel bis(8-hydroxyquinoline)phenolate-aluminum Complexes for Organic Light-emitting Diodes," Synthetic Metals, 2002, vol. 131, 1-3, pp. 1-5.

Extended European Search Report for Application No. 09848342.3, counterpart to U.S. Appl. No. 12/643,487; Jan. 23, 2013.

Extended European Search Report for Application No. 09849078.2, counterpart to U.S. Appl. No. 12/643,420; Jan. 11, 2013.

Extended European Search Report for Application No. 10746974.4, counterpart to U.S. Appl. No. 12/714,880; EPO; Nov. 5, 2012.

Extended European Search Report for Application No. 10778305.2, counterpart to U.S. Appl. No. 12/782,781; EPO; Nov. 5, 2012.

Extended European Search Report for Application No. EP 09844464.9, counterpart to U.S. Appl. No. 12/643,511; Oct. 26, 2012.

Extended European Search Report for Applicaton No. 09842844.4, counterpart to U.S. Appl. No. 12/643,486; Jan. 21, 2013.

* cited by examiner

ELECTROACTIVE MATERIALS

RELATED APPLICATION DATA

This application claims priority under 35 U.S.C. §119(e) from U.S. Provisional Application No. 61/166,400 filed on Apr. 3, 2009, which is incorporated by reference herein in its entirety.

BACKGROUND INFORMATION

1. Field of the Disclosure

The present disclosure relates to novel electroactive compounds. The disclosure further relates to electronic devices having at least one active layer comprising such an electroactive compound.

2. Description of the Related Art

In organic electroactive electronic devices, such as organic light emitting diodes ("OLED"), that make up OLED displays, the organic active layer is sandwiched between two electrical contact layers in an OLED display. In an OLED the organic electroactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used. In some cases the electroluminescent compound is present as a dopant in an electroactive host material. Devices that use electroluminescent materials frequently include one or more charge transport layers, which are positioned between an electroactive (e.g., light-emitting) layer and a contact layer (hole-injecting contact layer). A device can contain two or more contact layers. A hole transport layer can be positioned between the electroluminescent layer and the hole-injecting contact layer. The hole-injecting contact layer may also be called the anode. An electron transport layer can be positioned between the electroluminescent layer and the electron-injecting contact layer. The electron-injecting contact layer may also be called the cathode.

There is a continuing need for electroactive materials for use in electronic devices.

SUMMARY

There is provided a compound having at least two diarylamino moieties and having at least 10% deuteration.

There is also provided a compound having Formula I, Formula II, or Formula III:

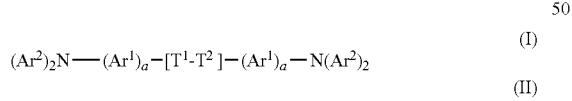
(I)

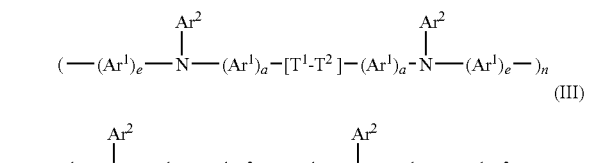
(II)
(III)

wherein:
Ar$^1$ is the same or different at each occurrence and is selected from the group consisting of phenylene, substituted phenylene, naphthylene, and substituted naphthylene;

Ar$^2$ is the same or different at each occurrence and is an aryl group;

M is the same or different at each occurrence and is a conjugated moiety;

T$^1$ and T$^2$ are independently the same or different at each occurrence and are conjugated moieties;

a is the same or different at each occurrence and is an integer from 1 to 6;

b, c, and d are mole fractions such that b+c+d=1.0, with the proviso that c is not zero, and at least one of b and d is not zero, and when b is zero, M comprises at least two triarylamine units;

e is the same or different at each occurrence and is an integer from 1 to 6; and n is an integer greater than 1;

wherein the compound has at least 10% deuteration.

There is also provided a compound comprising at least one fluorene moiety and at least two triarylamine moieties, wherein the compound has at least 10% deuteration.

There is also provided an electronic device having at least one layer comprising at least one of the abovedescribed compounds.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
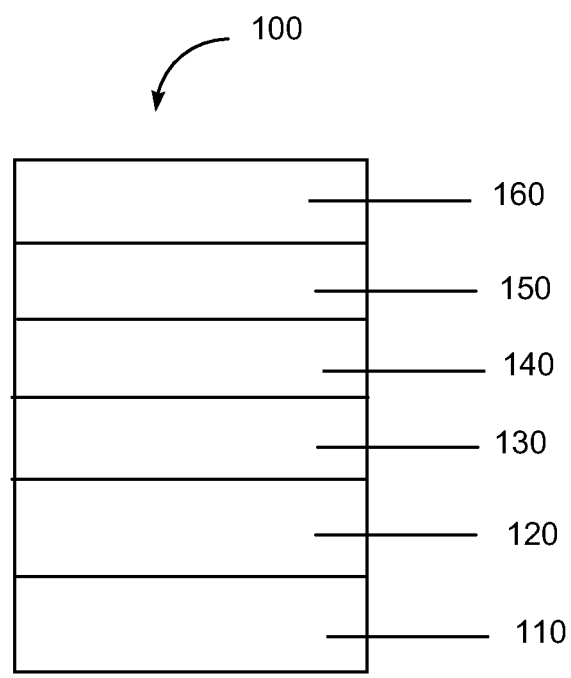
FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

There is provided a compound having at least two diarylamino moieties and having at least 10% deuteration.

There is also provided a compound having Formula I, Formula II, or Formula III:

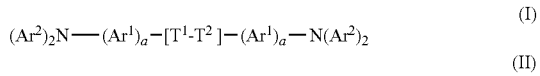
(I)

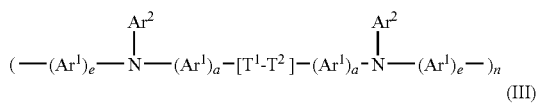
(II)
(III)

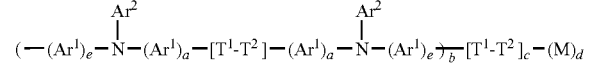

wherein:
Ar$^1$ is the same or different at each occurrence and is selected from the group consisting of phenylene, substituted phenylene, naphthylene, and substituted naphthylene;

$Ar^2$ is the same or different at each occurrence and is an aryl group;

M is the same or different at each occurrence and is a conjugated moiety;

$T^1$ and $T^2$ are independently the same or different at each occurrence and are conjugated moieties;

a is the same or different at each occurrence and is an integer from 1 to 6;

b, c, and d are mole fractions such that b+c+d=1.0, with the proviso that c is not zero, and at least one of b and d is not zero, and when b is zero, M comprises at least two triarylamine units;

e is the same or different at each occurrence and is an integer from 1 to 6; and n is an integer greater than 1;

wherein the compound has at least 10% deuteration.

There is also provided a compound comprising at least one fluorene moiety and at least two triarylamine moieties, wherein the compound has at least 10% deuteration.

There is also provided an electronic device having at least one layer comprising the above compound.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Electroactive Compound, the Electronic Device, and finally Examples.

1. Definitions and Clarification of Terms

Before addressing details of embodiments described below, some terms are defined or clarified.

As used herein, the term "aliphatic ring" is intended to mean a cyclic group that does not have delocalized pi electrons. In some embodiments, the aliphatic ring has no unsaturation. In some embodiments, the ring has one double or triple bond.

The term "alkoxy" refers to the group RO—, where R is an alkyl.

The term "alkyl" is intended to mean a group derived from an aliphatic hydrocarbon having one point of attachment, and includes a linear, a branched, or a cyclic group. The term is intended to include heteroalkyls. The term "hydrocarbon alkyl" refers to an alkyl group having no heteroatoms. The term "deuterated alkyl" is a hydrocarbon alkyl having at least one available H replaced by D. In some embodiments, an alkyl group has from 1-20 carbon atoms; in some embodiments, 1-10 carbon atoms. Examples of alkyl groups include methyl, ethyl, propyl, isopropyl, isobutyl, secbutyl, tertbutyl, pentyl, isopentyl, neopentyl, cyclopentyl, hexyl, cyclohexyl, isohexyl, ethylhexyl, tert-octyl and the like.

The term "aryl" is intended to mean a group derived from an aromatic hydrocarbon having one point of attachment. The term "aromatic compound" is intended to mean an organic compound comprising at least one unsaturated cyclic group having delocalized pi electrons. The term is intended include heteroaryls. The term "hydrocarbon aryl" is intended to mean aromatic compounds having no heteroatoms in the ring. The term aryl includes groups which have a single ring and those which have multiple rings which can be joined by a single bond or fused together. The term "deuterated aryl" refers to an aryl group having at least one available H bonded directly to the aryl replaced by D. The term "arylene" is intended to mean a group derived from an aromatic hydrocarbon having two points of attachment. In some embodiments, an aryl group has from 3-60 carbon atoms. Any suitable ring position of the aryl moiety may be covalently linked to the defined chemical structure. Examples of aryl moieties include, but are not limited to, phenyl, 1-naphthyl, 2-naphthyl, dihydronaphthyl, tetrahydronaphthyl, biphenyl. anthryl, phenanthryl, fluorenyl, indanyl, biphenylenyl, acenaphthenyl, acenaphthylenyl, and the like. In some embodiments, aryl groups have 6 to 60 carbon atoms; in some embodiments, 6 to 30 carbon atoms. The term is intended to include heteroaryl groups. Heteroaryl groups may have from 4-50 carbon atoms; in some embodiments, 4-30 carbon atoms.

The term "aryloxy" is intended to mean the group —OR, where R is aryl.

Unless otherwise indicated, all groups can be substituted or unsubstituted. An optionally substituted group, such as, but not limited to, alkyl or aryl, may be substituted with one or more substituents which may be the same or different. Suitable substituents include D, alkyl, aryl, nitro, cyano, —N($R^7$)($R^8$), halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, silyl, siloxane, thioalkoxy, —S(O)$_2$—N(R')(R"), —C(=O)—N(R')(R"), (R')(R")N-alkyl, (R')(R")N-alkoxyalkyl, (R')(R")N-alkylaryloxyalkyl, —S(O)$_s$-aryl (where s=0-2) or —S(O)$_s$-heteroaryl (where s=0-2). Each R' and R" is independently an optionally substituted alkyl, cycloalkyl, or aryl group. R' and R", together with the nitrogen atom to which they are bound, can form a ring system in certain embodiments. Substituents may also be crosslinking groups.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport material facilitate negative charge. Although light-emitting materials may also have some charge transport properties, the term "charge transport layer, material, member, or structure" is not intended to include a layer, material, member, or structure whose primary function is light emission.

The term "compound" is intended to mean an electrically uncharged substance made up of molecules that further include atoms, wherein the atoms cannot be separated from their corresponding molecules by physical means without breaking chemical bonds. The term is intended to include oligomers and polymers.

The term "conjugated moiety" is intended to mean a moiety having delocalized electrons. The delocalized electrons can be from alternating single and multiple carbon bonds and/or atoms with lone electron pairs.

The term "crosslinkable group" or "crosslinking group" is intended to mean a group than can lead to crosslinking via thermal treatment or exposure to radiation. In some embodiments, the radiation is UV or visible.

The term "deuterated" is intended to mean that at least one available H has been replaced by D. A compound that is X % deuterated, has X % of the available H replaced by D. A "deuterated analog" of a compound or group is the same compound or group having at least one available H replaced by D. A deuterated compound has deuterium present in at least 100 times the natural abundance level.

The term "electroactive" as it refers to a layer or a material, is intended to indicate a layer or material which electronically facilitates the operation of the device. Examples of active materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The prefix "fluoro" is intended to indicate that one or more hydrogens in a group has been replaced with fluorine.

The prefix "hetero" indicates that one or more carbon atoms has been replaced with a different atom. In some embodiments, the heteroatom is O, N, S, or combinations thereof.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The term "non-planar configuration" as it refers to $[T^1-T^2]$ in Formulae I-III herein, is intended to mean that the immediately adjacent groups in $T^1$ and $T^2$ are not oriented in the same plane.

The term "organic electronic device" or sometimes just "electronic device" is intended to mean a device including one or more organic semiconductor layers or materials.

The term "oxyalkyl" is intended to mean a heteroalkyl group having one or more carbons replaced with oxygens. The term includes groups which are linked via an oxygen.

The term "silyl" refers to the group $R_3Si-$, where R is H, D, C1-20 alkyl, fluoroalkyl, or aryl. In some embodiments, one or more carbons in an R alkyl group are replaced with Si. In some embodiments, the silyl groups are $(hexyl)_2Si(Me)CH_2CH_2Si(Me)_2-$ and $[CF_3(CF_2)_6CH_2CH_2]_2SiMe-$.

The term "siloxane" refers to the group $(RO)_3Si-$, where R is H, D, C1-20 alkyl, or fluoroalkyl.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics, 81st Edition* (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Electroactive Compound

The compound described herein has at least two diarylamino moieties and has at least 10% deuteration. In some embodiments, the compound is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated.

In some embodiments, the deuterated compound has Formula I, Formula II, or Formula III:

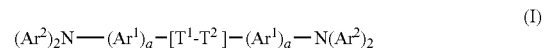

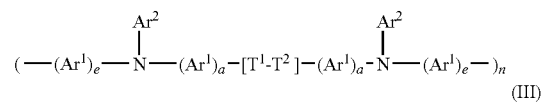

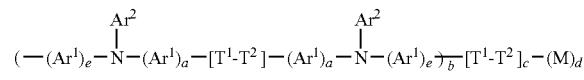

wherein:

$Ar^1$ is the same or different at each occurrence and is selected from the group consisting of phenylene, substituted phenylene, naphthylene, and substituted naphthylene;

$Ar^2$ is the same or different at each occurrence and is an aryl group;

M is the same or different at each occurrence and is a conjugated moiety;

$T^1$ and $T^2$ are independently the same or different at each occurrence and are conjugated moieties;

a is the same or different at each occurrence and is an integer from 1 to 6;

b, c, and d are mole fractions such that b+c+d=1.0, with the proviso that c is not zero, and at least one of b and d is not zero, and when b is zero, M comprises at least two triarylamine units;

e is the same or different at each occurrence and is an integer from 1 to 6; and n is an integer greater than 1;

wherein the compound is at least 10% deuterated.

In some embodiments of Formulae I-III, the deuteration is on a substituent group on an aryl ring. In some embodiments, the substituent group is selected from alkyl, aryl, alkoxy, and aryloxy. In some embodiments, the substituent groups are at least 10% deuterated. By this it is meant that at least 10% of all the available H bonded to C in all the substituent groups are replaced with D. In some embodiments, each substituent will have some D. In some embodiments, some, and not all of the substituent groups have D. In some embodiments, the substituent groups are at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated.

In some embodiments of Formulae I-III, the deuteration is on any one or more of the aryl groups $Ar^1$ and $Ar^2$. In this case, at least one of $Ar^1$ and $Ar^2$ is a deuterated aryl group. In some embodiments, $Ar^1$ and $Ar^2$ are at least 10% deuterated. By this it is meant that at least 10% of all the available H bonded to aryl C in $Ar^1$ and $Ar^2$ are replaced with D. In some embodiments, each aryl ring will have some D. In some embodiments, some, and not all of the aryl rings have D. In some embodiments, $Ar^1$ and $Ar^2$ are at least 20% deuterated; in some embodiments, at least 30% deuterated; in some embodiments, at least 40% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated.

In some embodiments of Formulae I-III, deuteration is present on the $[T^1\text{-}T^2]$ group. In some embodiments, both $T^1$ and $T^2$ are deuterated. In some embodiments, the $[T^1\text{-}T^2]$ group is at least 10% deuterated. By this it is meant that at least 10% of all the available H bonded to aryl in the $[T^1\text{-}T^2]$ group is replaced with D. In some embodiments, the $[T^1\text{-}T^2]$ group is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated.

In some embodiments of Formulae I-III, the deuteration is present on both the substituent groups and the $Ar^1$ and $Ar^2$ groups. In some embodiments of Formulae I-III, the deuteration is present on both the $[T^1\text{-}T^2]$ group and the $Ar^1$ and $Ar^2$ groups. In some embodiments of Formulae I-III, the deuteration is present on the substituent groups, the $[T^1\text{-}T^2]$ group, and the $Ar^1$ and $Ar^2$ groups.

In some embodiments, the compound of Formulae I-III is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated.

In some embodiments, at least one $Ar^1$ is a substituted phenyl with a substituent selected from the group consisting of alkyl, alkoxy, silyl, a substituent with a crosslinking group, and deuterated analogs thereof. In some embodiments, the substituent is deuterated. In some embodiments, a is 1-3. In some embodiments a is 1-2. In some embodiments, a is 1. In some embodiments, e is 1-4. In some embodiments, e is 1-3.

In some embodiments, e=1. In some embodiments, at least one $Ar^1$ has a substituent that has a crosslinking group.

In some embodiments, at least one of $Ar^2$ has Formula a

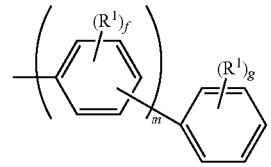

Formula a where:
$R^1$ is the same or different at each occurrence and is selected from the group consisting of D, alkyl, alkoxy, siloxane and, silyl; or adjacent $R^1$ groups may be joined to form an aromatic ring;
f is the same or different at each occurrence and is an integer from 0-4;
g is an integer from 0-5; and
m is an integer from 1 to 5.

In some embodiments, at least one of $Ar^2$ has Formula b:

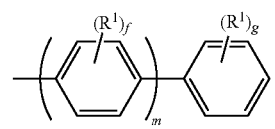

Formula b where:
$R^1$ is the same or different at each occurrence and is selected from the group consisting of D, alkyl, alkoxy, siloxane and, silyl; or adjacent $R^1$ groups may be joined to form an aromatic ring;
f is the same or different at each occurrence and is an integer from 0-4;
g is an integer from 0-5; and
m is an integer from 1 to 5.

In some embodiments of Formula a or b, at least one of f and g is not zero. In some embodiments, m=1-3.

In some embodiments, $Ar^2$ is selected from the group consisting of a group having Formula a, naphthyl, phenylnaphthyl, naphthylphenyl, and deuterated analogs thereof. In some embodiments, $Ar^2$ is selected from the group consisting phenyl, p-biphenyl, p-terphenyl, naphthyl, phenylnaphthyl, naphthylphenyl, and deuterated analogs thereof. In some embodiments, $Ar^2$ is selected from the group consisting of phenyl, biphenyl, terphenyl, and deuterated analogs thereof.

Any of the aromatic rings in Formulae I-III may be substituted at any position. The substituents may be present to improve one or more physical properties of the compound, such as solubility. In some embodiments, the substituents are selected from the group consisting of $C_{1-12}$ alkyl groups, $C_{1-12}$ alkoxy groups, silyl groups, and deuterated analogs thereof. In some embodiments, the alkyl groups are heteroalkyl groups. In some embodiments, the alkyl groups are fluoroalkyl groups. In some embodiments, at least one $Ar^2$ has an alkyl, alkoxy, silyl substituent, or deuterated analogs thereof. The substituents may be present to provide crosslinking capability. In some embodiments, crosslinking substituents are present on at least one $Ar^2$. In some embodiments, crosslinking substituents are present on at least one M moiety. In some embodiments, there is at least one substituent which includes a crosslinkable group. Examples of crosslinkable groups include, but are not limited to vinyl, acrylate, perfluorovinylether, 1-benzo-3,4-cyclobutane, siloxane, cyanate groups, cyclic ethers (epoxides), cycloalkenes, acetylenic groups, and deuterated analogs thereof.

In one embodiment, the crosslinkable group is vinyl. In some embodiments, the crosslinkable group is a deuterated vinyl group.

$T^1$ and $T^2$ are conjugated moieties. In some embodiments, $T^1$ and $T^2$ are aromatic moieties. In some embodiments, $T^1$ and $T^2$ are deuterated aromatic moieties. In some embodiments, $T^1$ and $T^2$ are selected from the group consisting of phenylene, napthylene, anthracenyl groups, and deuterated analogs thereof.

In some embodiments, the $T^1$-$T^2$ group introduces non-planarity into the backbone of the compound. The moiety in $T^1$ that is directly linked to a moiety in $T^2$ is linked such that the $T^1$ moiety is oriented in a plane that is different from the moiety in $T^2$ to which it is linked. Although other parts of the $T^1$ unit, for example, substituents, may lie in one or more different planes, it is the plane of the linking moiety in $T^1$ and the linking moiety in $T^2$ in the compound backbone that provide the non-planarity. Because of the non-planar $T^1$-$T^2$ linkage, the compounds are chiral. In general, they are formed as racemic mixtures. The compounds can also be in enantiomerically pure form. The non-planarity can be viewed as the restriction to free rotation about the $T^1$-$T^2$ bond. Rotation about that bond leads to racemization. The half-life of racemization for $T^1$-$T^2$ is greater than that for an unsubstituted biphenyl. In some embodiments, the half-life or racemization is 12 hours or greater at 20° C.

In some embodiments, [$T^1$-$T^2$] is a substituted biphenylene group, deuterated analog thereof. The term "biphenylene" is intended to mean a biphenyl group having two points of attachment to the compound backbone. The term "biphenyl" is intended to mean a group having two phenyl units joined by a single bond. The biphenylene group can be attached at one of the 2,3-, 4-, or 5-positions and one of the 2',3'-, 4'-, or 5'-positions. The substituted biphenylene group has at least one substitutent in the 2-position. In some embodiments, the biphenylene group has substituents in at least the 2- and 2'-positions.

In some embodiments, [$T^1$-$T^2$] is a binaphthylene group, or deuterated analog thereof. The term "binaphthylene" is intended to mean a binapthyl group having 2 points of attachment to the compound backbone. The term "binaphthyl" is intended to mean a group having two naphthalene units joined by a single bond. In some embodiments, the binaphthylene group is a 1,1'-binaphthylene, which is attached to the compound backbone at one of the 3-, 4-, 5-, 6, or 7-positions and one of the 3'-, 4'-, 5'-, 6', or 7'-positions. This is illustrated below, where the dashed lines represent possible points of attachment.

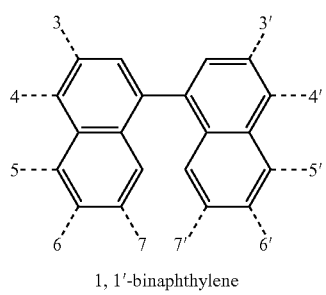

1, 1'-binaphthylene

In some embodiments, the binaphthylene group is a 1,2'-binaphthylene having at least one substituent at the 8- or 9'-position, and which is attached to the compound backbone at one of the 3-, 4-, 5-, 6, or 7-positions and one of the 4'-, 5'-, 6'-, 7', or 8'-positions. This is illustrated below, where the dashed lines represent possible points of attachment and at least one R represents a substituent.

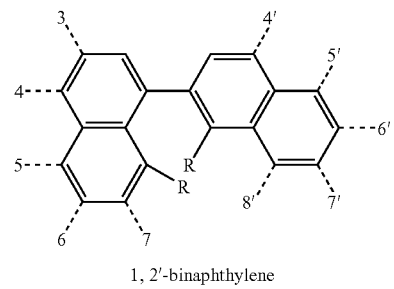

1, 2'-binaphthylene

In some embodiments, the binaphthylene group is a 2,2'-binaphthylene having at least one substituent at the 8- or 9'-position, and which is attached to the compound backbone at one of the 4-, 5-, 6-, 7, or 8-positions and one of the 4'-, 5'-, 6'-, 7', or 8'-positions. This is illustrated below, where the dashed lines represent possible points of attachment and at least one R represents a substituent.

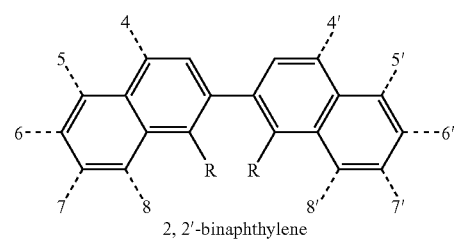

2, 2'-binaphthylene

In some embodiments, [$T^1$-$T^2$] is a phenylene-naphthylene group, or deuterated analog thereof. In some embodiments, [$T^1$-$T^2$] is a phenylene-1-naphthylene group, which is attached to the compound backbone at one of the 3-, 4-, or 5-positions in the phenylene and one of the 3-, 4-, or 5-positions of the naphthylene. In some embodiments, [$T^1$-$T^2$] is a phenylene-2-naphthylene group, which is attached to the compound backbone at one of the 3-, 4-, or 5-positions in the phenylene and one of the 4-, 5-, 6-, 7-, or 8-positions of the naphthylene.

In some embodiments, the biphenylene, binaphthylene, and phenylene-naphthylene groups are substituted at one or more positions.

In some embodiments, [$T^1$-$T^2$] is selected from one of the following:

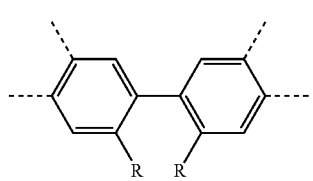

-continued

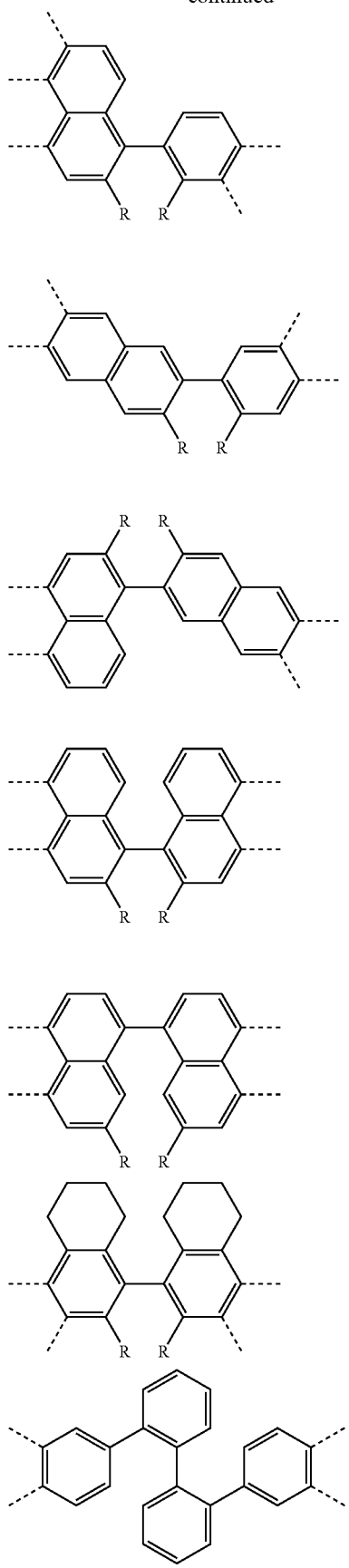

-continued

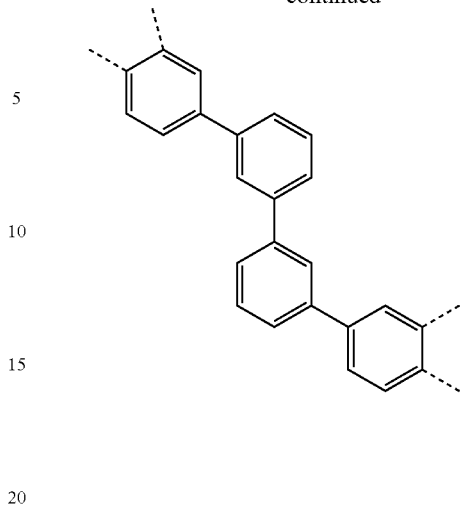

and deuterated analogs thereof, where R is the same or different and is selected from the group consisting of alkyl, aryl, alkoxy, aryloxy, fluoroalkyl, fluoroaryl, fluoroaryloxy fluoroalkyloxy, oxyalkyl, alkenyl groups, silyl, siloxane and crosslinking groups. The dashed line represents a possible point of attachment to the compound backbone. In some embodiments, R is a $C_{1-10}$ alkyl or alkoxy; in some embodiments, a $C_{3-8}$ branched alkyl or alkoxy. In some embodiments, the two R groups are joined together to form a non-aromatic ring.

In some embodiments, [$T^1$-$T^2$] is a 1,1-binaphthylene group, or deuterated analog thereof, which is attached to the compound backbone at the 4 and 4' positions, referred to as 4,4'-(1,1-binaphthylene). In some embodiments, the 4,4'-(1,1-binaphthylene) is the only isomer present. In some embodiments, two or more isomers are present. In some embodiments, the 4,4'-(1,1-binaphthylene) is present with up to 50% by weight of a second isomer. In some embodiments, the second isomer is selected from the group consisting of 4,5'-(1,1-binaphthylene), 4,6'-(1,1-binaphthylene), and 4,7'-(1,1-binaphthylene).

Formula III represents a copolymer in which there is at least one [$T^1$-$T^2$] moiety and at least one other conjugated moiety, where the overall polymer is at least 10% deuterated. In some embodiments, the deuteration is in the first monomeric unit, with the subscript "b". In some embodiments, the deuteration is in the second monomeric unit, with the subscript "c". In some embodiments, the deuteration is in the third monomeric unit, with the subscript "d". In some embodiments, the deuteration is in two monomeric units. In some embodiments, one of the two monomeric units is the first monomeric unit. In some embodiments, the deuteration is in all three monomeric units.

In some embodiments, c is at least 0.4. In some embodiments, c is in the range of 0.4 to 0.6. The copolymers can be random, alternating, or block copolymers. In some embodiments, M comprises triarylamine units. In some embodiments, M is an aromatic group. In some embodiments, M is an aromatic unit having a crosslinkable substituent. The amount of M having a crosslinkable substituent is generally between 4 and 20 mole percent.

Some non-limiting examples of compounds having Formula I include Compounds A and B below.
Compound A:
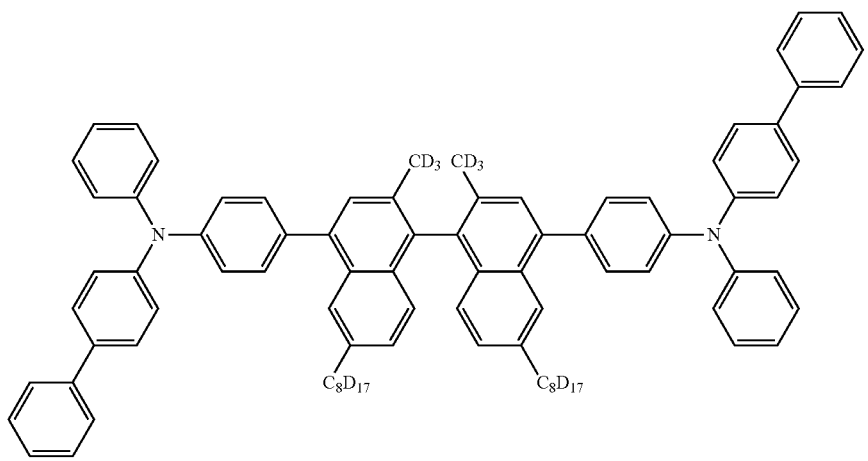
Compound B:
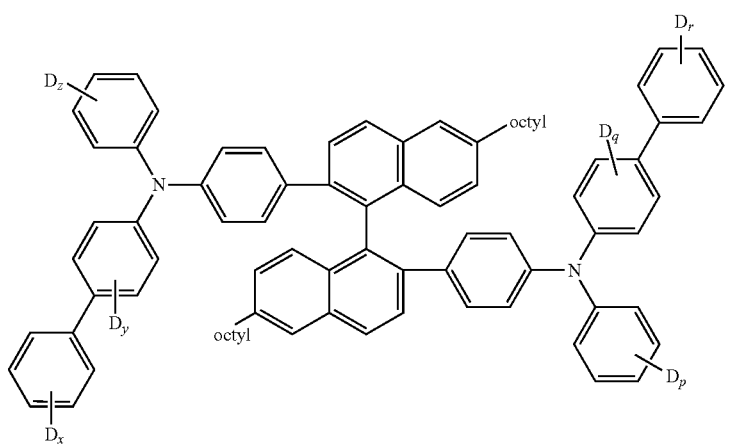
where x + y + z + p + q + r = 20-28
Some non-limiting examples of compounds having Formula II include Compounds C through H4 below.
Compound C
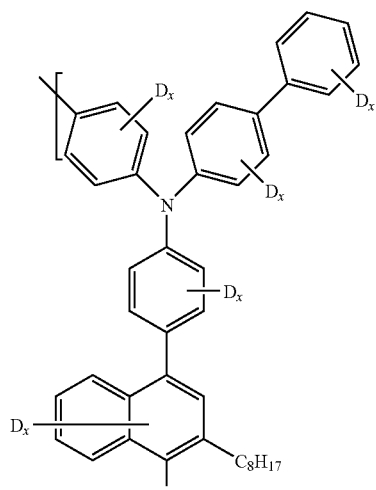

-continued
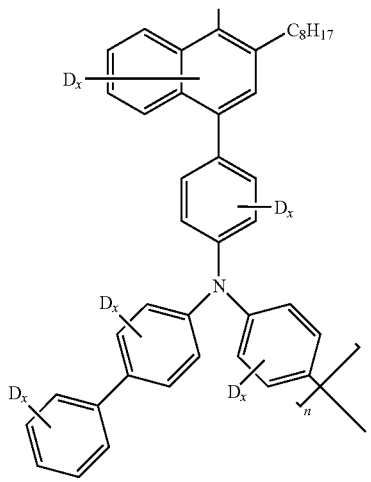
where x is 0-5 and Σ(x) = 10-44
Compound D:
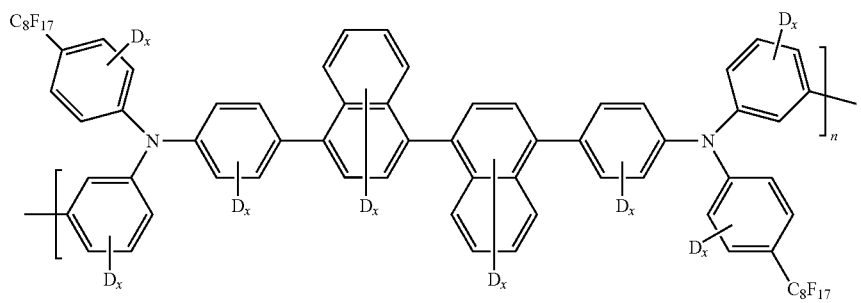
where x is 0-6 and Σ(x) = 8-36
Compound E:
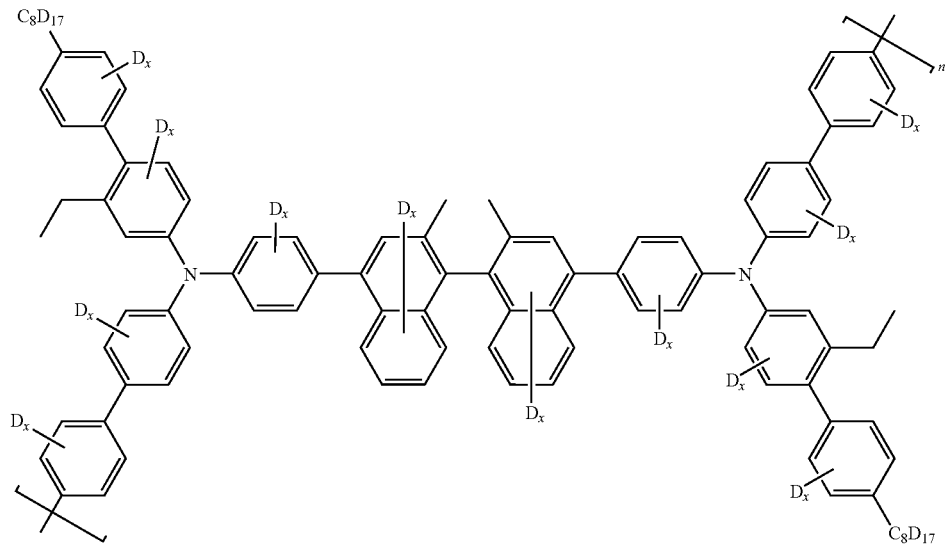
where x is 0-5 and Σ(x) = 10-50

Compound F:
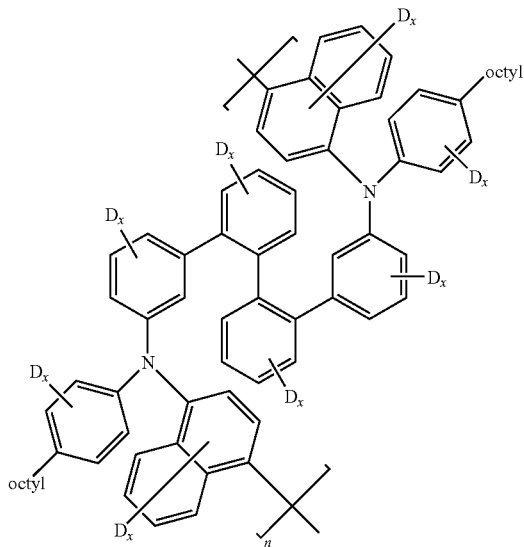
where x is 0-6 and Σ(x) = 8-36
Compound G:
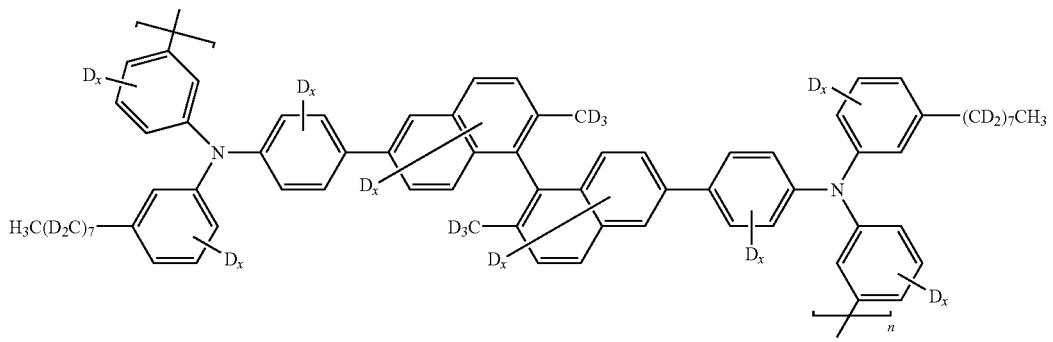
where x is 0-6 and Σ(x) = 8-36
Compound H1-H4:
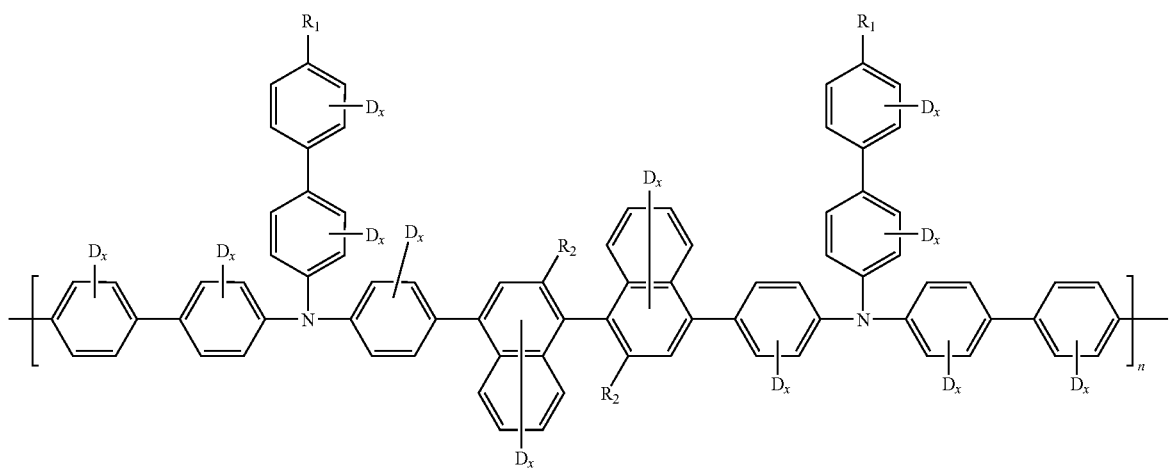
compound H1: $R_1 = D_y$-pentyl; $R_2 = D_y$-butyl
compound H2: $R_1 = D_y$-heptyl; $R_2 = D_y$-octyl
compound H3: $R_1 = D_y$-propyl; $R_2 = D_y$-octyl
compound H4: $R_1 = D_y$-octyl; $R_2 = D_y$-methyl
where x is 0-5 and Σ(x) = 10-50
y is 0-17 and Σ(y) = 0-32

Some non-limiting examples of compounds having Formula III include Compounds I through N below.
Compound I:
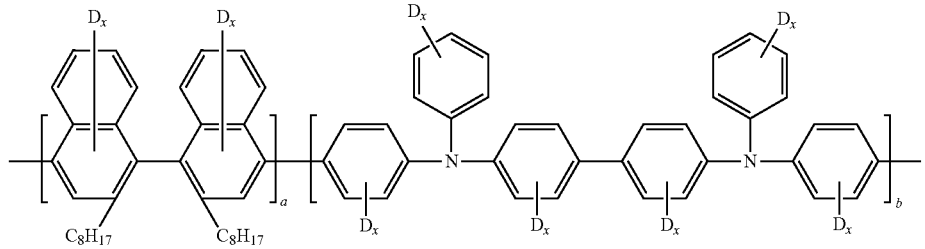
where a = 0.4-0.8
b = 0.2-0.6
x is 0-5 and Σ(x) = 10-36
Compound J:
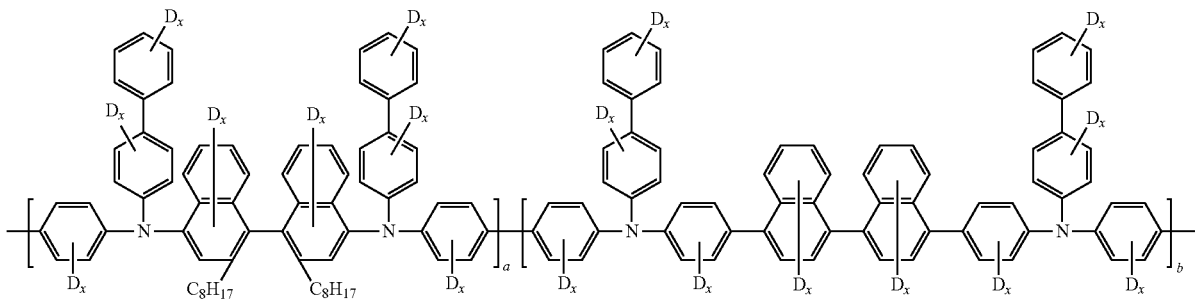
where a = 0.3 to 0.7
b = 0.3 to 0.7
x is 0-5 and Σ(x) = 20-80
Compound K:
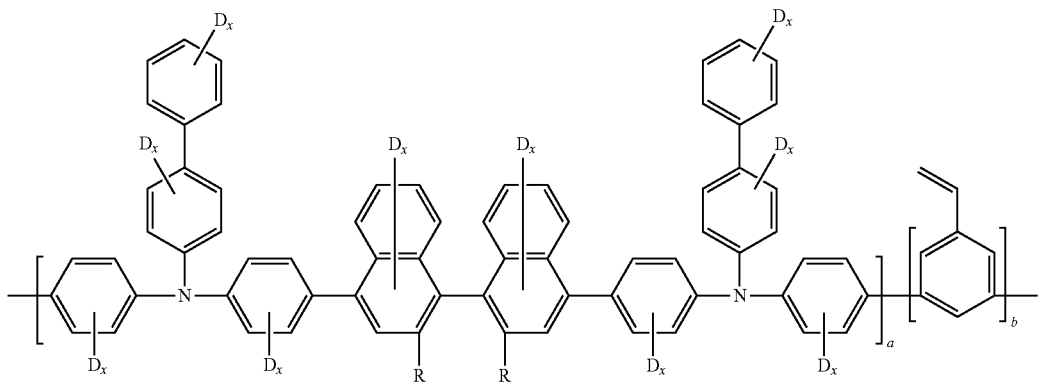
compound K-1: R = $C_8D_{17}$
compound K-2: R = $C_8H_{17}$
where a = 0.8 to 0.95
b = 0.05 to 0.2
x is 0-5 and Σ(x) = 10-44

Compound L:
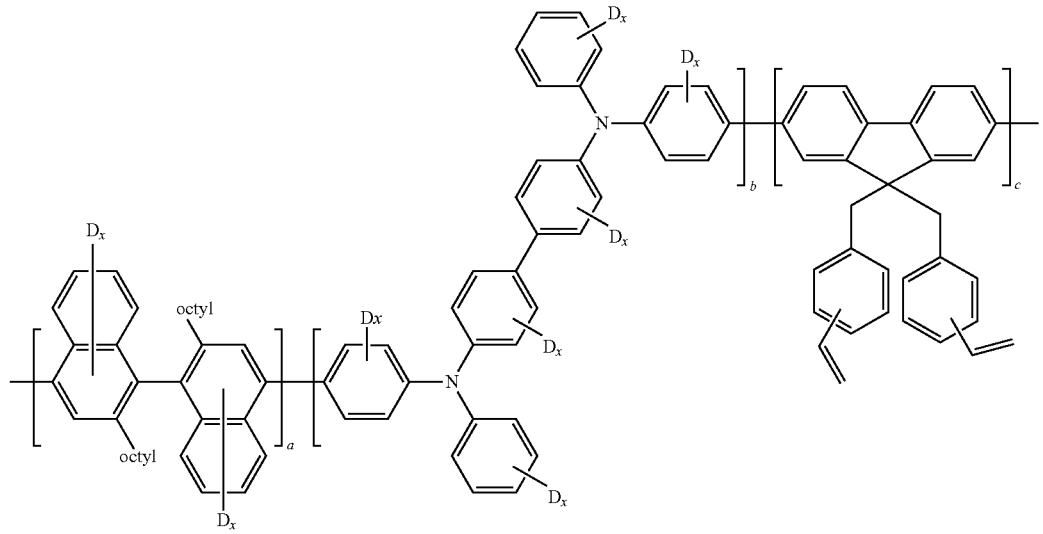
where a = 0.3-0.7
b = 0.3-0.5
c = 0.1-0.2
x is 0-5 and Σ(x) = 10-36
Compound M:
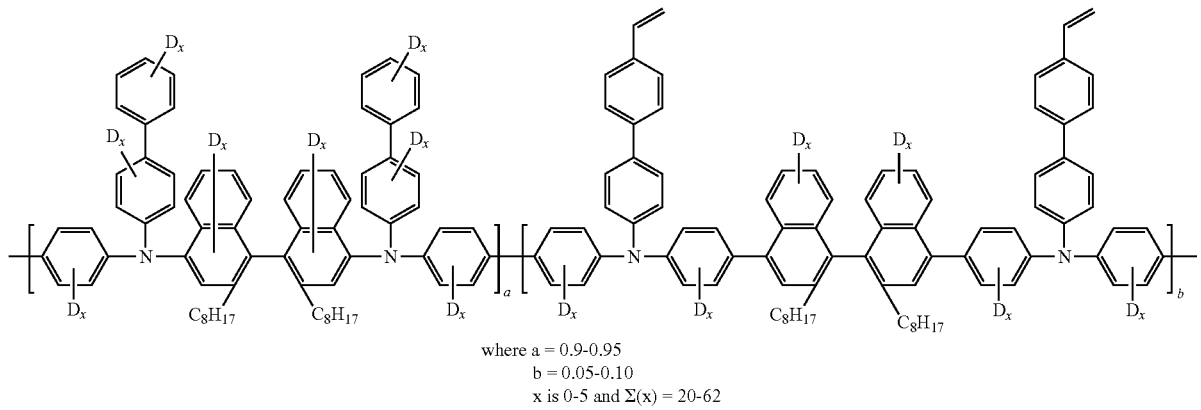
where a = 0.9-0.95
b = 0.05-0.10
x is 0-5 and Σ(x) = 20-62
Compound N:
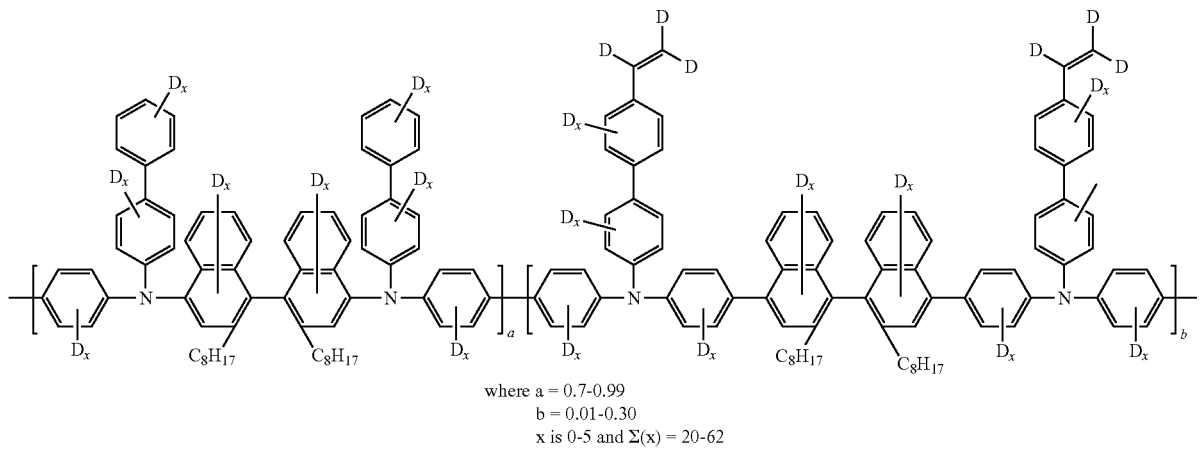
where a = 0.7-0.99
b = 0.01-0.30
x is 0-5 and Σ(x) = 20-62

In some embodiments, the deuterated compound has at least one fluorene moiety and at least two triarylamine moieties. In some embodiments, deuteration is present on the fluorene moiety. In some embodiments, deuteration is present on at least one triarylamine moiety. In some embodiments, dueteration is present on both fluorene and triarylamine moieties.

Any of the aromatic rings in the fluorene moiety or the triarylamine moiety may be substituted at any position. The substituents may be present to improve one or more physical properties of the compound, such as solubility. In some embodiments, the substituents are selected from the group consisting of $C_{1-12}$ alkyl groups, $C_{1-12}$ alkoxy groups, silyl groups, and deuterated analogs thereof. In some embodiments, the alkyl groups are heteroalkyl groups. In some embodiments, the alkyl groups are fluoroalkyl groups. In some embodiments, at least one aryl ring has a substituent selected from the group consisting of alkyl, alkoxy, silyl, a crosslinking substituent, and deuterated analogs thereof.

In some embodiments, the compound is a polymer. The polymer can be formed by copolymerizing at least one monomer having a fluorene group with at least one monomer having triarylamine groups. Alternatively the polymer can be formed from a single monomer having both fluorene and triarylamine groups. Other aromatic monomeric units may also be present in the polymer, as discussed above for M. The deuteration may be present on the fluorene and/or triarylamine monomeric units, as discussed above. Any of the aromatic rings in the fluorene moiety or the triarylamine moiety may be substituted at any position, as discussed above.

Some non-limiting examples of compounds having fluorene and triarylamine moieties include Compounds O and P below.

Compound O:

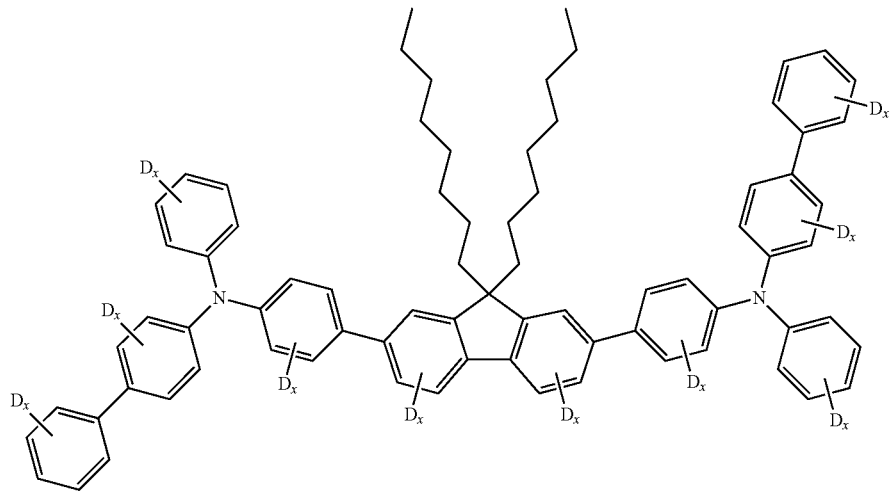

where x is 0-5 and $\Sigma(x) = 15\text{-}42$

Compound P:

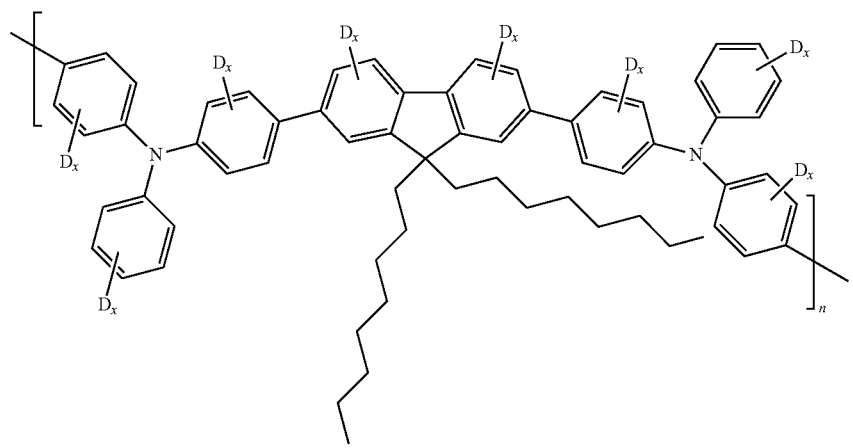

where: n is an integer greater than 1;
x is 0-5 and $\Sigma(x) = 10\text{-}32$

The non-deuterated analog compounds can be made using any technique that will yield a C—C or C—N bond. A variety of such techniques are known, such as Suzuki, Yamamoto, Stille, and Pd- or Ni-catalyzed C—N couplings. The synthesis of non-deuterated analog compounds has been described in, for example, published PCT applications WO 2008/024378, WO 2008/024379, and WO 2009/067419. The new deuterated compound can then be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum dichloride. Exemplary preparations are given in the Examples. The level of deuteration can be determined by NMR analysis and by mass spectrometry, such as Atmospheric Solids Analysis Probe Mass Spectrometry (ASAP-MS).

The compounds described herein can be formed into films using liquid deposition techniques. Surprisingly and unexpectedly, these compounds have greatly improved properties when compared to analogous non-deuterated compounds. Electronic devices including an active layer with the compounds described herein, have greatly improved lifetimes. In addition, the lifetime increases are achieved in combination with high quantum efficiency and good color saturation. Furthermore, the deuterated compounds described herein have greater air tolerance than the non-deuterated analogs. This can result in greater processing tolerance both for the preparation and purification of the materials and in the formation of electronic devices using the materials.

The new deuterated compounds described herein have utility as hole transport materials, as electroluminescent materials, and as hosts for electroluminescent materials. In some embodiments, the new deuterated compounds are used as a first hole transport layer in combination with a second hole transport layer. The new compounds have hole mobilities and HOMO/LUMO energies similar to efficient small molecule hole transport compounds such as N,N'-diphenyl-N,N'-bis(3-methylphenyl)-[1,1'-biphenyl]-4,4'-diamine (TPD) and N,N'-bis(naphthalen-1-yl)-N,N'-bis-(phenyl)benzidine (α-NPB). Compounds such as TPD and NPD generally must be applied using a vapor deposition technique.

3. Electronic Devices

Organic electronic devices that may benefit from having one or more layers comprising at least one compound as described herein include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a transistor or diode). Other uses for the compositions according to the present invention include coating materials for memory storage devices, antistatic films, biosensors, electrochromic devices, solid electrolyte capacitors, energy storage devices such as a rechargeable battery, and electromagnetic shielding applications.

One illustration of an organic electronic device structure is shown in FIG. 1. The device 100 has a first electrical contact layer, an anode layer 110 and a second electrical contact layer, a cathode layer 160, and an electroactive layer 140 between them. Adjacent to the anode is a hole injection layer 120. Adjacent to the hole injection layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160. When two or more hole transport layers are present, they may be the same or different in com-position, and the same or different in thickness. When two or more electron transport layers are present, they may be the same or different in composition, and the same or different in thickness.

Layers 120 through 150 are individually and collectively referred to as the active layers.

In one embodiment, the different layers have the following range of thicknesses: anode 110, 500-5000 Å, in one embodiment 1000-2000 Å; hole injection layer 120, 50-3000 Å, in one embodiment 200-1000 Å; hole transport layer 130, 50-2000 Å, in one embodiment 200-1000 Å; electroactive layer 140, 10-2000 Å, in one embodiment 100-1000 Å; layer 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used.

Depending upon the application of the device 100, the electroactive layer 140 can be a light-emitting layer that is activated by an applied voltage (such as in a light-emitting diode or light-emitting electrochemical cell), or a layer of material that responds to radiant energy and generates a signal with or without an applied bias voltage (such as in a photo-detector). Examples of photodetectors include photoconductive cells, photoresistors, photoswitches, phototransistors, and phototubes, and photovoltaic cells, as these terms are described in Markus, John, *Electronics and Nucleonics Dictionary,* 470 and 476 (McGraw-Hill, Inc. 1966).

In some embodiments, the new deuterated compounds are useful as hole transport materials in layer 130. In some embodiments, at least one additional layer includes a deuterated material. In some embodiments, the additional layer is the hole injection layer 120. In some embodiments, the additional layer is the electroactive layer 140. In some embodiments, the additional layer is the electron transport layer 150.

In some embodiments, the new deuterated compounds are useful as host materials for electroluminescent materials in electroactive layer 140. In some embodiments, the emissive material is also deuterated. In some embodiments, at least one additional layer includes a deuterated material. In some embodiments, the additional layer is the hole injection layer 120. In some embodiments, the additional layer is the hole transport layer 130. In some embodiments, the additional layer is the electron transport layer 150

In some embodiments, the new deuterated compounds are useful as electron transport materials in layer 150. In some embodiments, at least one additional layer includes a deuterated material. In some embodiments, the additional layer is the hole injection layer 120. In some embodiments, the additional layer is the hole transport layer 130. In some embodiments, the additional layer is the electroactive layer 140.

In some embodiments, an electronic device has deuterated materials in any combination of layers selected from the group consisting of the hole injection layer, the hole transport layer, the electroactive layer, and the electron transport layer.

In some embodiments, the devices have additional layers to aid in processing or to improve functionality. Any or all of these layers can include deuterated materials. In some embodiments, all the organic device layers comprise deuterated materials. In some embodiments, all the organic device layers consist essentially of deuterated materials.

The other layers in the device can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

In some embodiments, the device further comprises a hole injection layer between the anode and the layer comprising the new polymer. The term "hole injection layer" is intended to mean a layer comprising electrically conductive or semiconductive materials and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules, and may be in the form of solutions, dispersions, suspensions, emulsions, colloidal mixtures, or other compositions. The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like. The hole injection layer can comprise charge transfer compounds, and the like, such as copper phthalocyanine and the tetrathiafulvalene-tetracyanoquinodimethane system (TTF-TCNQ). In one embodiment, the hole injection layer is made from a dispersion of a conducting polymer and a colloid-forming polymeric acid. Such materials have been described in, for example, published U.S. patent applications 2004-0102577, 2004-0127637, and 2005-205860.

In some embodiments, hole transport layer 120 comprises the new deuterated electroactive compound described herein. In some embodiments, hole transport layer 120 consists essentially of the new deuterated electroactive compound described herein. In some embodiments, layer 120 comprises other hole transport materials. Examples of other hole transport materials for layer 120 have been summarized for example, in Kirk Othmer Encyclopedia of Chemical Technology, Fourth Edition, Vol. 18, p. 837 860, 1996, by Y. Wang. Both hole transporting molecules and polymers can be used. Commonly used hole transporting molecules include, but are not limited to: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl 4-N,N-diphenylaminostyrene (TPS), p-(diethylamino)benzaldehyde diphenylhydrazone (DEH), triphenylamine (TPA), bis[4 (N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N' tetrakis(4-methylphenyl)-(1,1'-biphenyl)-4,4'-diamine (TTB), N,N'-Bis(naphthalen-1-yl)-N,N'-bis-(phenyl)benzidine (α-NPB), and porphyrinic compounds, such as copper phthalocyanine. Commonly used hole transporting polymers include, but are not limited to, polyvinylcarbazole, (phenylmethyl)polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. Examples of crosslinkable hole transport polymers can be found in, for example, published US patent application 2005-0184287 and published PCT application WO 2005/052027. In some embodiments, the hole transport layer is doped with a p-dopant, such as tetrafluorotetracyanoquinodimethane and perylene-3,4,9,10-tetracarboxylic-3,4,9,10-dianhydride.

Depending upon the application of the device, the electroactive layer 140 can be a light-emitting layer that is activated by an applied voltage (such as in a light-emitting diode or light-emitting electrochemical cell), a layer of material that responds to radiant energy and generates a signal with or without an applied bias voltage (such as in a photodetector). In one embodiment, the electroactive material is an organic electroluminescent ("EL") material. Any EL material can be used in the devices, including, but not limited to, small molecule organic fluorescent compounds, fluorescent and phosphorescent metal complexes, conjugated polymers, and mixtures thereof. Examples of fluorescent compounds include, but are not limited to, chrysenes, pyrenes, perylenes, rubrenes, coumarins, anthracenes, thiadiazoles, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. In some cases the small molecule fluorescent or organometallic materials are deposited as a dopant with a host material to improve processing and/or electronic properties. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In some embodiments, the electroluminescent material is a cyclometalated complex of iridium. In some embodiments, the complex has two ligands selected from phenylpyridines, phenylquinolines, and phenylisoquinolines, and a third ligand with is a β-dienolate. The ligands may be unsubstituted or substituted with F, D, alkyl, CN, or aryl groups.

In some embodiments, the electroluminescent material is a polymer selected from the group consisting of poly(phenylenevinylenes), polyfluorenes, and polyspirobifluorenes.

In some embodiments, the electroluminescent material is selected from the group consisting of a non-polymeric spirobifluorene compound and a fluoranthene compound.

In some embodiments, the electroluminescent material is a compound having aryl amine groups.

In some embodiments, host materials are selected from the group consisting of hole transport materials, electron transport materials, and combinations thereof.

The new deuterated compounds of Formulae I-III are useful as hosts for electroluminescent materials in layer 140. The compounds can be used alone, or in combination with a second host material. The new deuterated compounds can be used as a host for materials with any color of emission.

In some embodiments, the electroactive layer consists essentially of a host material having one of Formulae I-III and one or more electroluminescent compounds. In some embodiments, the electroluminescent material is selected from the group consisting of amino-substituted chrysenes and amino-substituted anthracenes.

Electron transport layer 150 can function both to facilitate electron transport, and also serve as a hole injection layer or confinement layer to prevent quenching of the exciton at layer interfaces. Preferably, this layer promotes electron mobility and reduces exciton quenching. Examples of electron transport materials which can be used in the optional electron transport layer 150, include metal chelated oxinoid compounds, including metal quinolate derivatives such as tris(8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport layer further comprises an n-dopant. Examples of n-dopants include, but are not limited to Cs or other alkali metals.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, $Li_2O$, Cs-containing organometallic compounds, CsF, $Cs_2O$, and $Cs_2CO_3$ can also be deposited between the organic layer and the cathode layer to lower the operating voltage. This layer may be referred to as an electron injection layer.

The choice of materials for each of the component layers is preferably determined by balancing the goals of providing a device with high device efficiency with device operational lifetime. Other layers may also be present in the device. There may be one or more hole injection and/or hole transport layers between the hole injection layer and the organic active layer. There may be one or more electron transport layers and/or electron injection layers between the organic active layer and the cathode.

The device can be prepared by a variety of techniques, including sequentially depositing the individual layers on a suitable substrate. Substrates such as glass and polymeric films can be used. Conventional vapor deposition techniques can be used, such as thermal evaporation, chemical vapor deposition, and the like. Alternatively, the organic layers can be applied by liquid deposition using suitable solvents. The liquid can be in the form of solutions, dispersions, or emulsions. Typical liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing. any conventional coating or printing technique, including but not limited to spin-coating, dip-coating, roll-to-roll techniques, ink jet printing, screen-printing, gravure printing and the like.

The new deuterated electroactive compounds described herein can be applied by liquid deposition from a liquid composition. The term "liquid composition" is intended to mean a liquid medium in which a material is dissolved to form a solution, a liquid medium in which a material is dispersed to form a dispersion, or a liquid medium in which a material is suspended to form a suspension or an emulsion.

In one embodiment, the device has the following structure, in order: anode, hole injection layer, hole transport layer, electroactive layer, electron transport layer, electron injection layer, cathode. In one embodiment, the anode is made of indium tin oxide or indium zinc oxide.

In one embodiment, the hole injection layer comprises a conducting polymer selected from the group consisting of polythiophenes, polyanilines, polypyrroles, copolymers thereof, and mixtures thereof. In one embodiment, the hole injection layer comprises a complex of a conducting polymer and a colloid-forming polymeric acid.

In one embodiment, the hole transport layer comprises the new deuterated compound described herein. In one embodiment, the hole transport layer comprises a compound having triarylamine or triarylmethane groups. In one embodiment, the hole transport layer comprises a material selected from the group consisting of TPD, MPMP, NPB, CBP, and mixtures thereof, as defined above.

In one embodiment, the electroactive layer comprises an electroluminescent material and a host material. The host can be a charge transport material. In one embodiment, the host is the new deuterated electroactive compound described herein. In one embodiment, the electroactive layer further comprises a second host material.

In one embodiment, the electron transport layer comprises a metal complex of a hydroxyaryl-N-heterocycle. In one embodiment, the hydroxyaryl-N-heterocycle is unsubstituted or substituted 8-hydroxyquinoline. In one embodiment, the metal is aluminum. In one embodiment, the electron transport layer comprises a material selected from the group consisting of tris(8-hydroxyquinolinato)aluminum, bis(8-hydroxyquinolinato)(4-phenylphenolato)aluminum, tetrakis(8-hydroxyquinolinato)zirconium, tetrakis(8-hydroxyquinolinato)hafnium, and mixtures thereof. In one embodiment, the electron injection layer is LiF or $Li_2O$. In one embodiment, the cathode is Al or Ba/Al. In one embodiment, there is an electron transport layer comprising a material selected from the group consisting of tris(8-hydroxyquinolinato)aluminum, bis(8-hydroxyquinolinato)(4-phenylphenolato)aluminum, tetrakis(8-hydroxyquinolinato)zirconium, tetrakis(8-hydroxyquinolinato)hafnium, and mixtures thereof, and an electron injection layer comprising LiF or $Li_2O$.

In one embodiment, the device is fabricated by liquid deposition of the hole injection layer, the hole transport layer, and the electroactive layer, and by vapor deposition of the electron transport layer, the electron injection layer, and the cathode.

In one embodiment, the device is fabricated by vapor deposition of the hole injection layer, the hole transport layer, and the electroactive layer, the electron transport layer, the electron injection layer, and the cathode.

In one embodiment, the device is fabricated by vapor deposition of some of the organic layers, and liquid deposition of some of the organic layers. In one embodiment, the device is fabricated by liquid deposition of the hole injection layer, and vapor deposition of all of the other layers Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

EXAMPLES

The concepts described herein will be further described in the following examples, which do not limit the scope of the invention described in the claims.

Comparative Example A

This example illustrates the preparation of a non-deuterated compound, Comparative A, according to the scheme below.

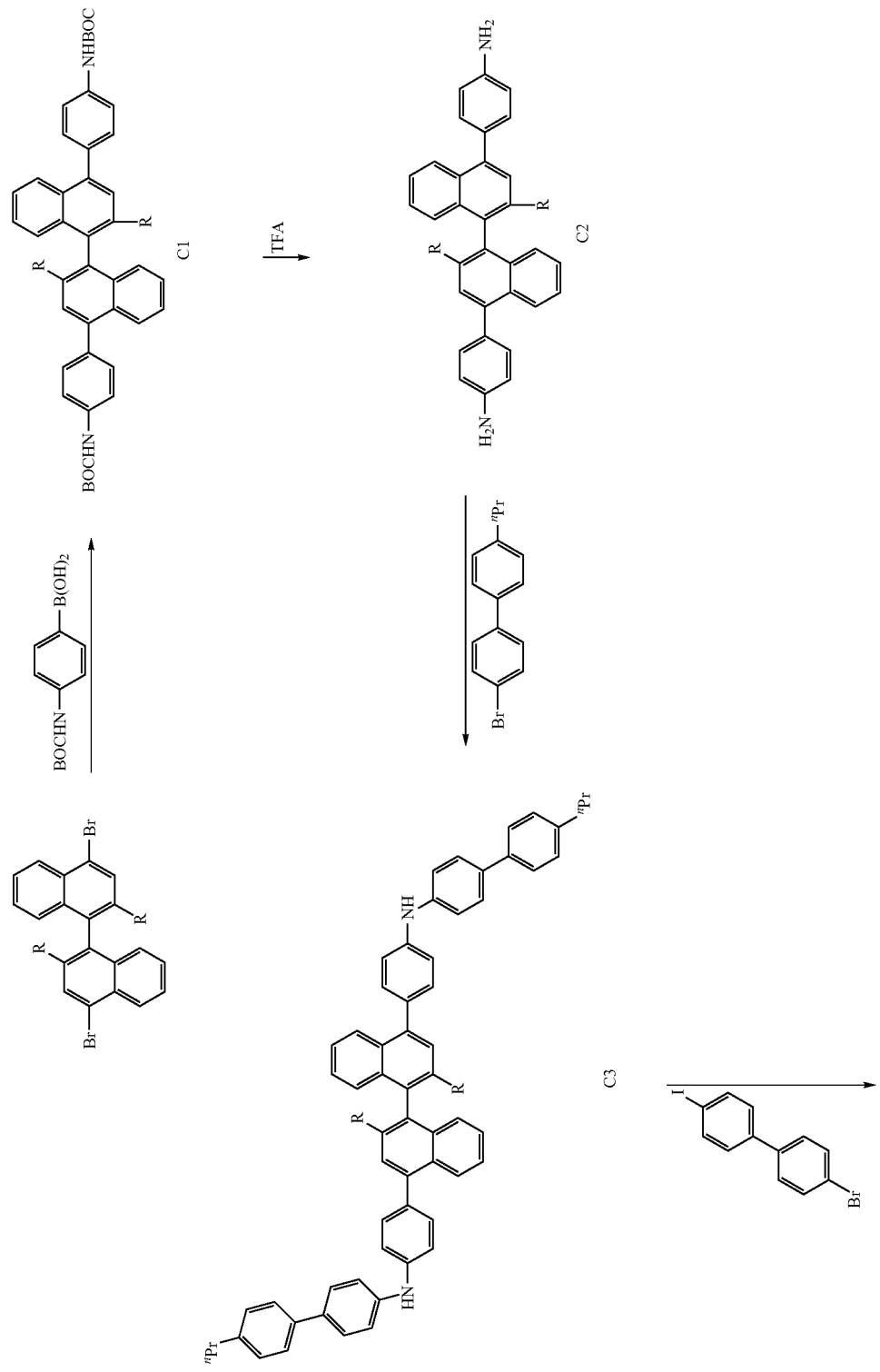

-continued
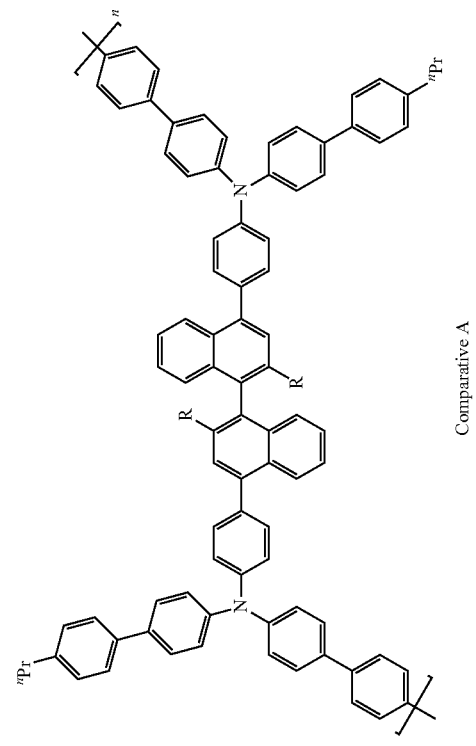
Comparative A
↑ Ni(COD)₂
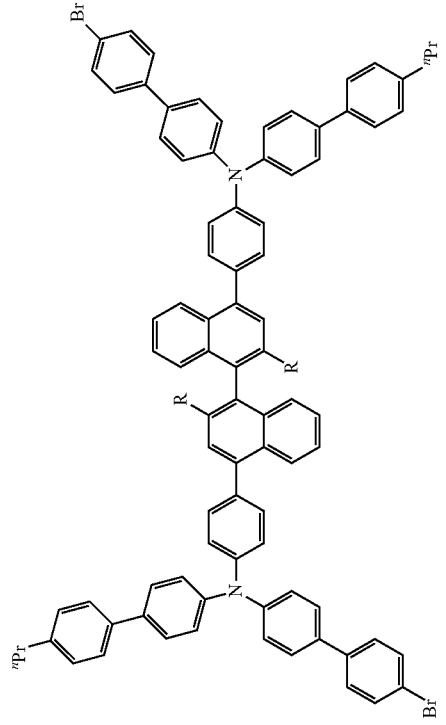
C4
R = ⁿOctyl

Synthesis of Comparative A.
Part 1—Intermediate Compound C1:

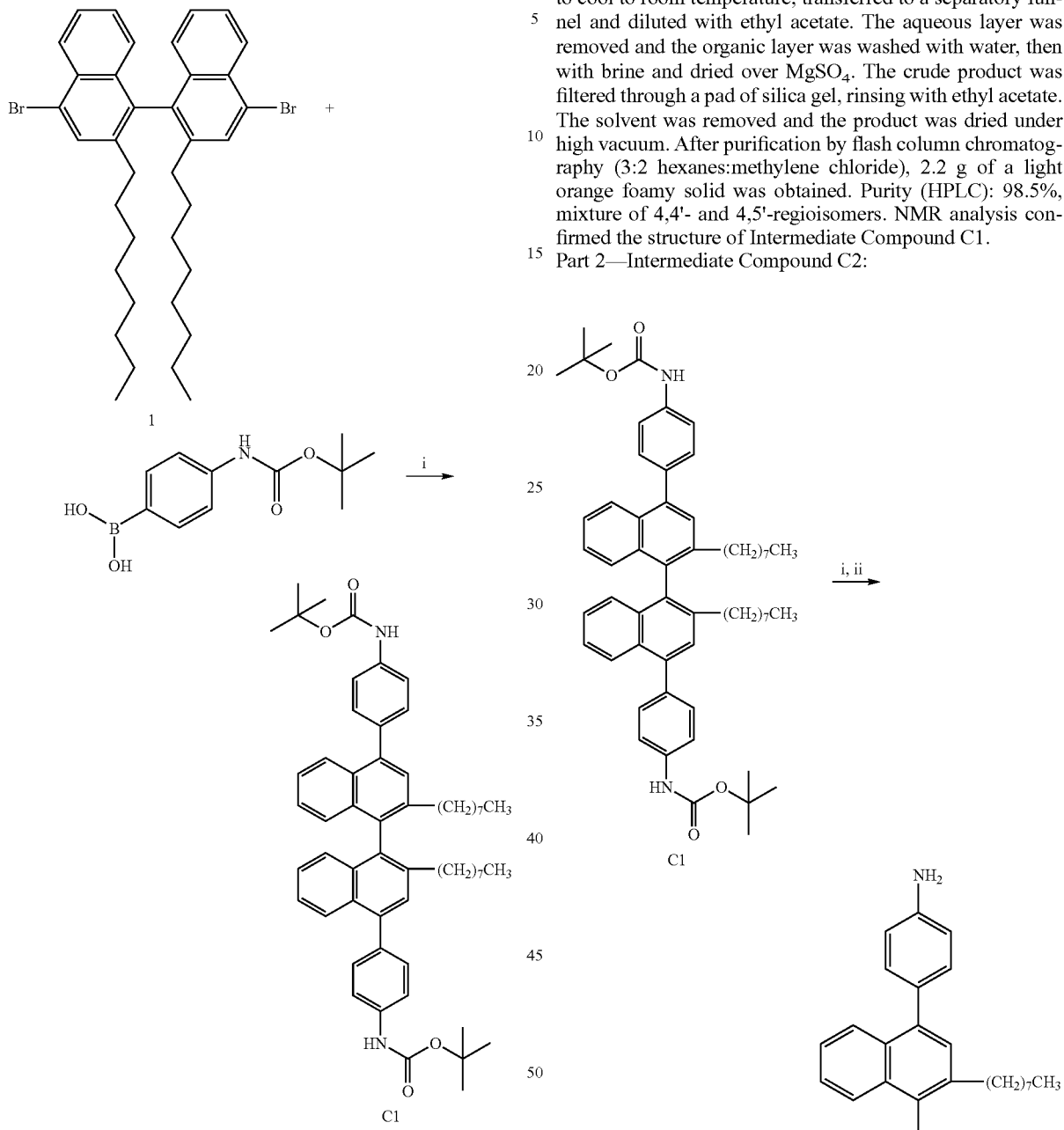

i- 5 mol % (Ph$_3$P)$_4$Pd(0)], Aliquat(R) 336, 1M Na$_2$CO$_3$, toluene, 90° C.

Compound 1 (4.0 g, 6.3 mmol) was dissolved in 60 mL toluene in a 2 neck 200 mL septum-sealed round bottom. 4-[(tert-Butoxycarbonyl)amino]benzeneboronic acid (3.72 g, 15.7 mmol), Aliquat® 336 (0.5 g) and sodium carbonate (3.33 g, 31.4 mmol) were added. The mixture was sparged with nitrogen and the reaction flask was fitted with a reflux condenser and nitrogen inlet-outlet. In a nitrogen purged glovebox, tetrakistriphenylphosphine (363 mg, 5.00 mol %) and anhydrous toluene (10 mL) were combined in a round bottom flask. The flask was sealed with a septum and removed from the glovebox. The catalyst suspension was added to the reaction mixture via a cannula. Water (30 mL) was added to the reaction vessel via syringe. The nitrogen sparge was removed and replaced with a nitrogen blanket. The reaction mixture was heated at 90° C. for 3 h. The reaction was allowed to cool to room temperature, transferred to a separatory funnel and diluted with ethyl acetate. The aqueous layer was removed and the organic layer was washed with water, then with brine and dried over MgSO$_4$. The crude product was filtered through a pad of silica gel, rinsing with ethyl acetate. The solvent was removed and the product was dried under high vacuum. After purification by flash column chromatography (3:2 hexanes:methylene chloride), 2.2 g of a light orange foamy solid was obtained. Purity (HPLC): 98.5%, mixture of 4,4'- and 4,5'-regioisomers. NMR analysis confirmed the structure of Intermediate Compound C1.

Part 2—Intermediate Compound C2:

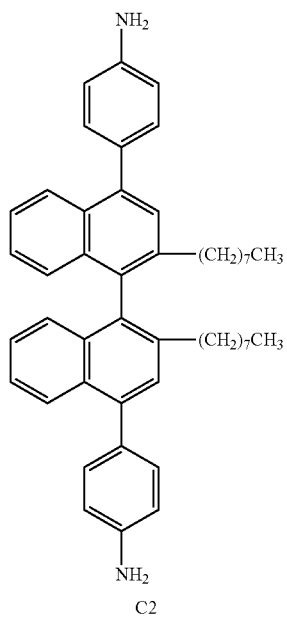

Conditions: i- TFA, CH$_2$Cl$_2$; ii- 10% NaHCO$_3$

Intermediate Compound C1 (2.2 g, 2.5 mmol) was dissolved in 40 mL methylene chloride in a 250 mL round bottom flask equipped with a magnetic stirrer and a nitrogen inlet-outlet. Trifluoroacetic acid (2.9 g, 25 mmol) was added and the reaction was allowed to stir for 16 h. The solvent and trifluoroacetic acid were removed by rotary evaporation and the product was taken up in diethyl ether. The diethyl ether solution was washed with saturated sodium bicarbonate (2×), water and brine. The ether layer was dried over MgSO4, filtered and concentrated on a rotary evaporator. The product was dried under high vacuum to yield 1.7 g (100%) of a light orange foamy solid. Purity (HPLC): 94.7%. NMR analysis confirmed the structure of Intermediate Compound C2.

Part 3—Synthesis of Intermediate Compound C3:

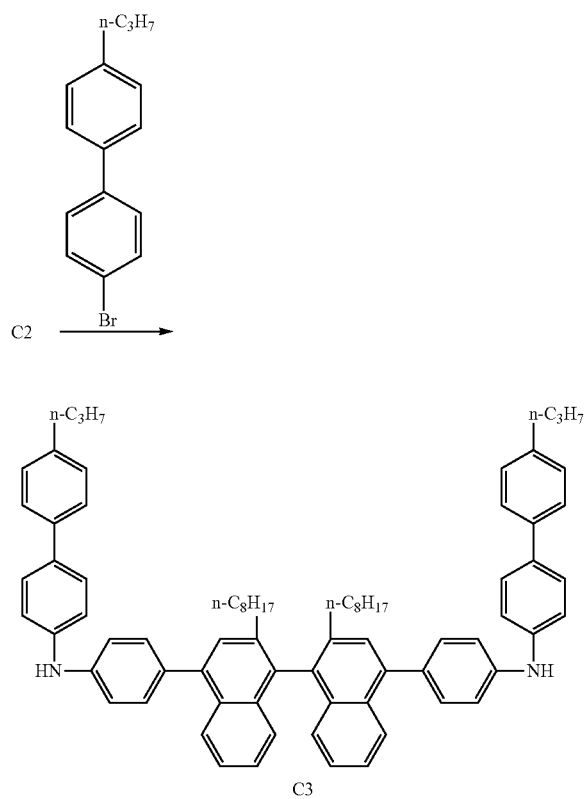

Under an atmosphere of nitrogen, compound C2 (2.0 g, 3.03 mmol), 4-bromo-4'-propylbiphenyl (1.67 g, 6.05 mmol), tris(dibenzylideneacetone)dipalladium(0) (139 mg, 5 mol %), tri-t-butylphosphine (61 mg, 10 mol %) and toluene (27 mL) were combined. Sodium t-butoxide (0.872 g, 9.08 mmol) was added and the reaction was stirred at room temperature for 40 h. 4-bromo-4'-propylbiphenyl (250 mg, 0.91 mmol), tris(dibenzylideneacetone)dipalladium(0) (55 mg, 2 mol %), tri-t-butylphosphine (25 mg, 4 mol %) and sodium t-butoxide (291 mg, 3.03 mmol) were then added. After another 23 h, the reaction mixture was filtered through a pad of Celite, rinsing with toluene. The solution was concentrated on a rotary evaporator and dried under vacuum. The product was purified by medium pressure liquid chromatography on silica gel (0-40% methylene chloride gradient in hexanes) to give 1.70 g (53% yield) of a white solid. NMR analysis confirmed the structure of Intermediate Compound C3 as a mixture of 4,4'- and 4,5'-regioisomers. Purity (UPLC): 97.8%.

Part 4—Synthesis of Intermediate 4-bromo-4'-iodobiphenyl:

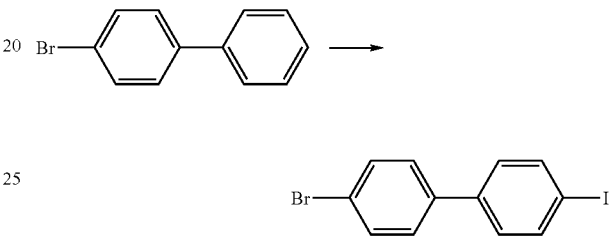

A 4-neck one liter round bottom flask equipped with mechanical stirrer, thermometer and reflux condenser topped with nitrogen bubbler inlet was charged with 4-bromobiphenyl (23.31 g, 100 mmol) in acetic acid (400 mL), sulfuric acid (10 mL) and water (20 mL). To this stirring mixture was added iodic acid (4.84 g, 27.5 mmol) followed immediately by addition of iodine chips (11.17 g, 44.0 mmol). The reaction flask was immersed in a preheated tri(ethylene glycol) heating bath and heated at 65° C. internal temperature. After 30 min the bath temperature was increased such that the internal temperature raised to 85° C. after 20 min. Heating at this temperature was continued for 4.5 hours at which point UPLC analysis showed the reaction to be complete. After stirring overnight at room temperature the reaction mixture was vacuum filtered through a coarse fritted funnel and the solids were rinsed with water. The resulting white solid (32.1 g, 89% yield) had mp 177-179° C. and was used without further purification in the next step. NMR analysis confirmed the structure 4-bromo-4'-iodobiphenyl. Purity (UPLC): >99%.

Part 5—Synthesis of Intermediate Compound C4:

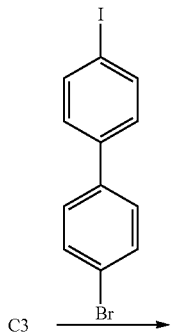

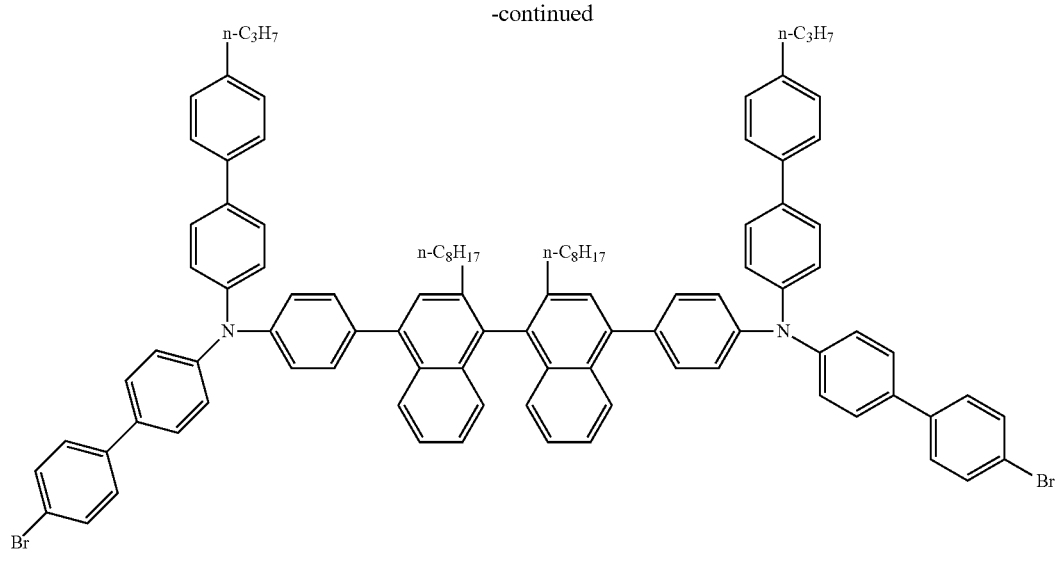

C4

In a nitrogen purged glovebox, a 3-neck round bottom flask equipped with a magnetic stirrer, thermometer and reflux condenser topped with a gas inlet adaptor in the closed position was charged with C3 (1.70 g, 1.62 mmol), 4-bromo-4'-iodobiphenyl (2.62 g, 7.29 mmol), tris(dibenzylideneacetone)dipalladium(0) (178 mg, 12 mol %), bis(diphenylphosphinoferrocene) (215 mg, 24 mol %) and toluene (30 mL) through the open neck. Sodium t-butoxide (0.342 g, 3.56 mmol) was added, the open neck was capped and the reaction vessel was removed from the glovebox. A nitrogen bubbler hose was fitted to the gas inlet adaptor and the stopcock was turned to the open position under a slight positive pressure of nitrogen. The reaction was heated at reflux in a tri(ethylene glycol) bath. The reaction was heated at reflux. After 16 h, the reaction was cooled to room temperature and tris(dibenzylideneacetone)dipalladium(0) (178 mg, 12 mol %), bis(diphenylphosphino)ferrocene (215 mg, 24 mol %) and sodium t-butoxide (342 mg, 3.56 mmol) was added to the reaction mixture. After additional 2 h at reflux, the reaction mixture was cooled to room temperature. After 72 h at room temperature the reaction mixture was filtered through a pad of Celite, rinsing with toluene. The filtrate was concentrated by rotary evaporation. The crude product was dried under high vacuum and purified by medium pressure liquid chromatography on silica gel (0-35% methylene chloride gradient in hexanes) to give 1.42 g (58% yield) of a white solid. NMR analysis confirmed the structure of Intermediate Compound C4 as a mixture of 4,4'- and 4,5'-regioisomers. Purity (UPLC): 98.7%.

Part 6—Synthesis of Comparative A.

All operations were carried out in a nitrogen purged glovebox unless otherwise noted. Monomer C4 (0.756 g, 0.50 mmol) was added to a scintillation vial and dissolved in 20 mL toluene. A clean, dry 50 mL Schlenk tube was charged with bis(1,5-cyclooctadiene)nickel(0) (0.278 g, 1.01 mmol). 2,2'-Dipyridyl (0.58 g, 1.01 mmol) and 1,5-cyclooctadiene (0.109 g, 1.01 mmol) were weighed into a scintillation vial and dissolved in 5 mL N,N'-dimethylformamide. The solution was added to the Schlenk tube. The Schlenk tube was inserted into an aluminum block and the block was heated and stirred on a hotplate/stirrer at a setpoint that resulted in an internal temperature of 60° C. The catalyst system was held at 60° C. for 30 minutes. The monomer solution in toluene was added to the Schlenk tube and the tube was sealed. The polymerization mixture was stirred at 60° C. for four hours. The Schlenk tube was then removed from the block and allowed to cool to room temperature. The tube was removed from the glovebox and the contents were poured into a solution of conc. HCl/MeOH (1.5% v/v conc. HCl). After stirring for 45 minutes, the polymer was collected by vacuum filtration and dried under high vacuum. The polymer was purified by successive precipitations from toluene into HCl/MeOH (1 v/v conc. HCl), MeOH, toluene (CMOS grade), and 3-pentanone. A white, fibrous polymer (0.53 g, 78.4% yield) was obtained. The molecular weight of the polymer was determined by GPC (THF mobile phase, polystyrene standards): $M_w$=512,983; $M_n$=136,936; PDI=3.75. NMR analysis confirmed the structure of Comparative A.

Example 1

This example illustrates the preparation of a deuterated electroactive compound, Compound H3, where $R^1$=n-propyl, $R^2$=n-octyl, y=0 and $\Sigma(x)$=42:

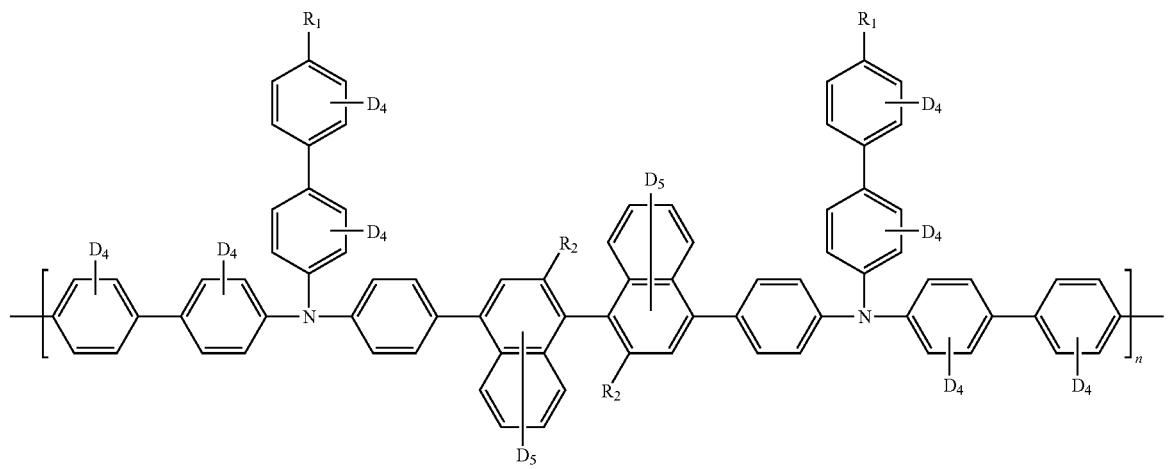
The compound is made according to the scheme below.

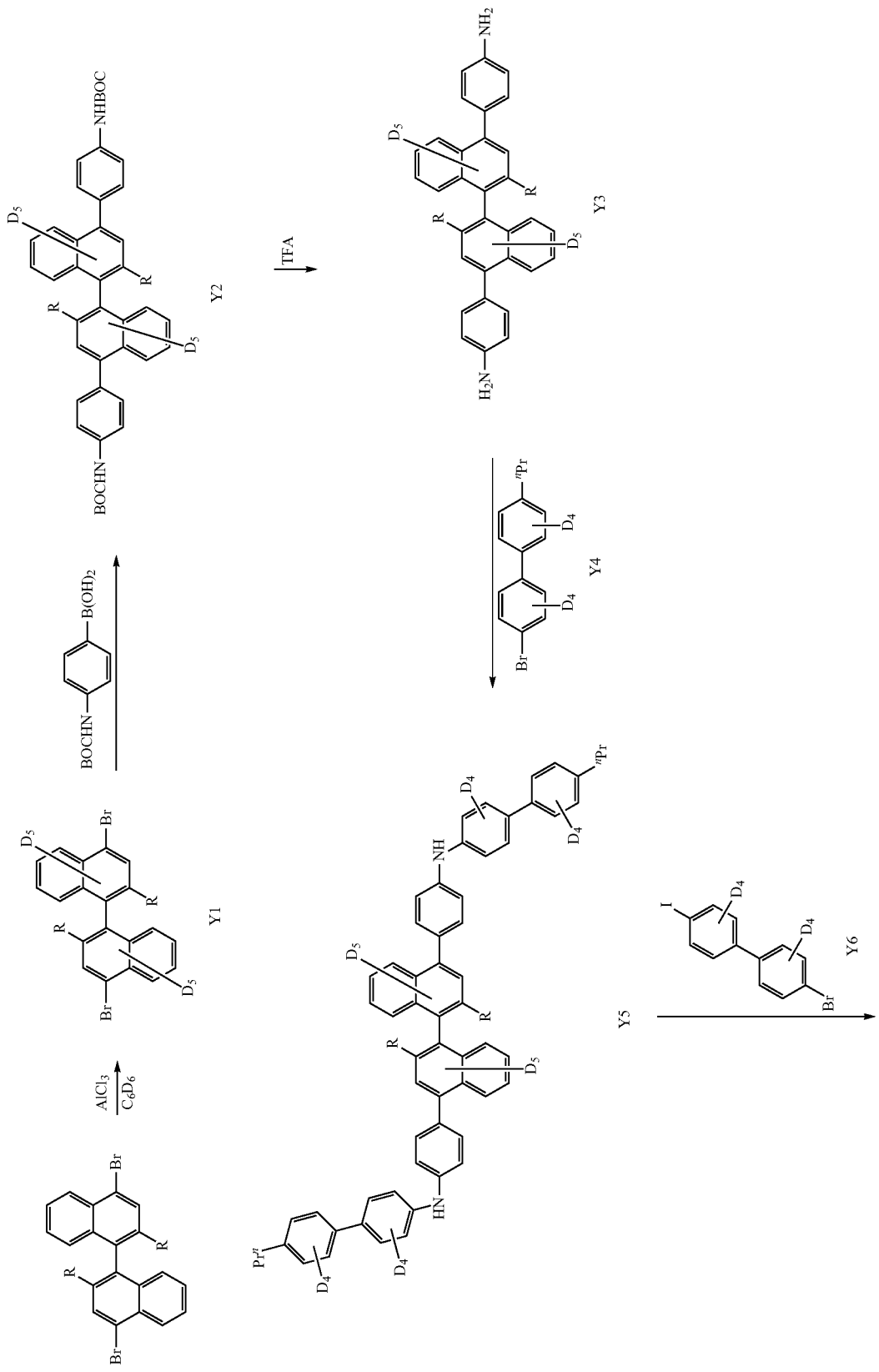

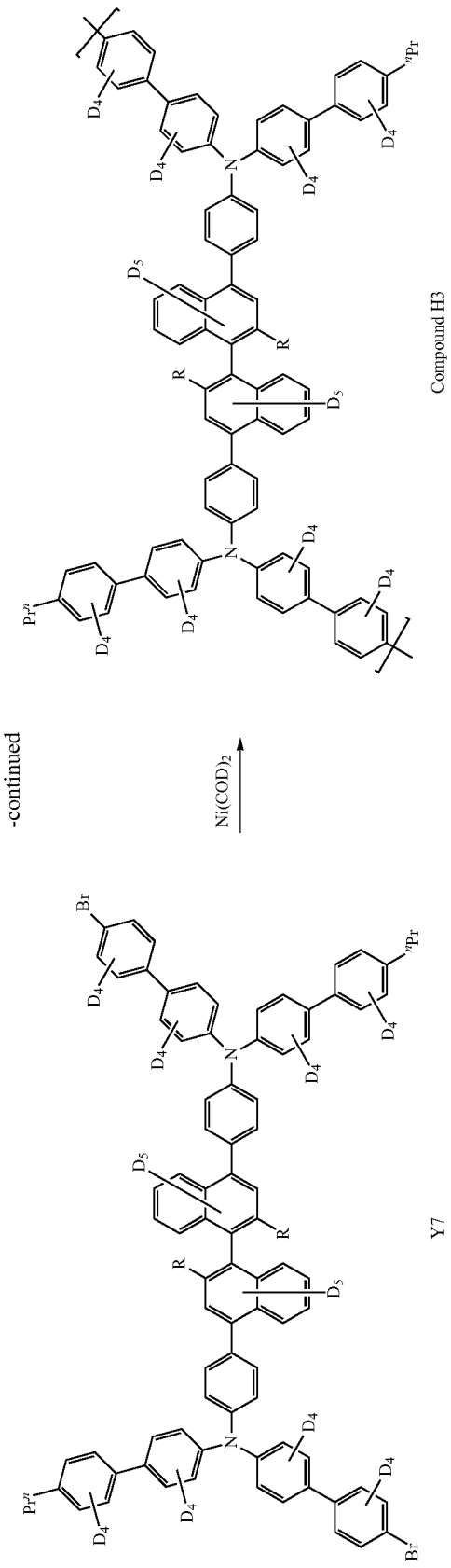

Synthesis of Intermediate Compound Y1:

Under an atmosphere of nitrogen, $AlCl_3$ (0.17 g, 1.29 mmol) was added to a $C_6D_6$ (100 mL) solution of 2,2'-dioctyl-4,4'-dibromo-1,1'-binaphthylene (2.328 g, 3.66 mmol). The resulting mixture was stirred at room temperature for 30 minutes after which $D_2O$ (50 mL) was added. The layers were separated followed by washing the water layer with $CH_2Cl_2$ (2×30 mL). The combined organic layers were dried over magnesium sulfate and the volatiles were removed by rotary evaporation. The crude product was purified via column chromatography. Compound Y1 was obtained (1.96 g) as a white powder.

Synthesis of Intermediate Compound Y2:

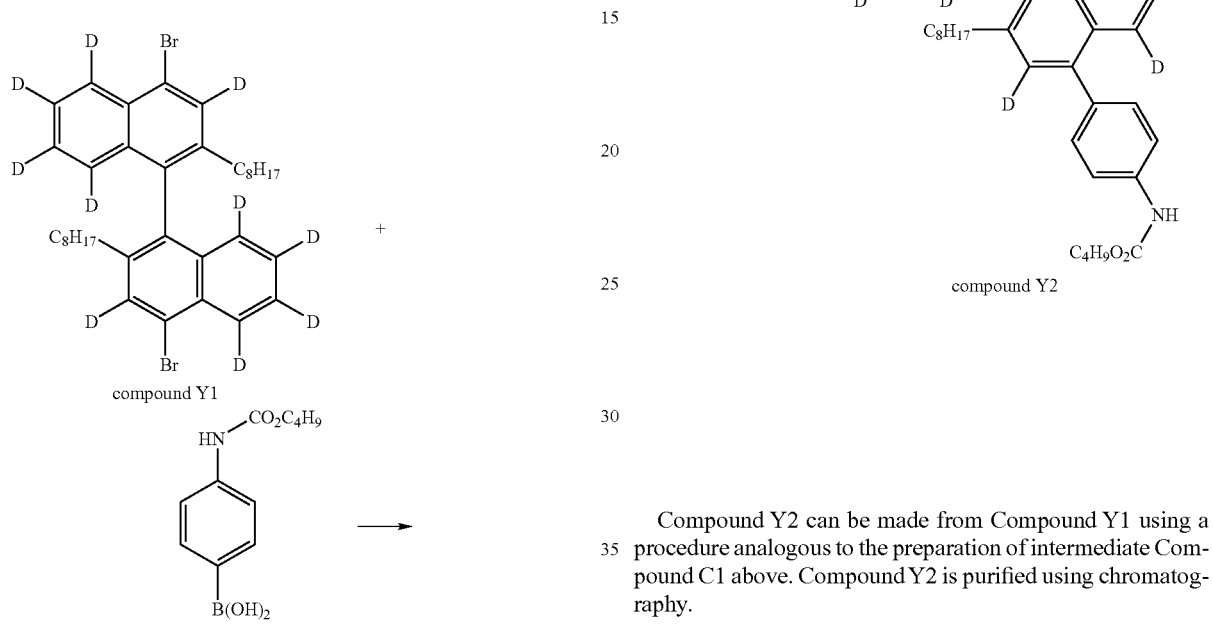

compound Y2

Compound Y2 can be made from Compound Y1 using a procedure analogous to the preparation of intermediate Compound C1 above. Compound Y2 is purified using chromatography.

Synthesis of Intermediate Compound Y3:

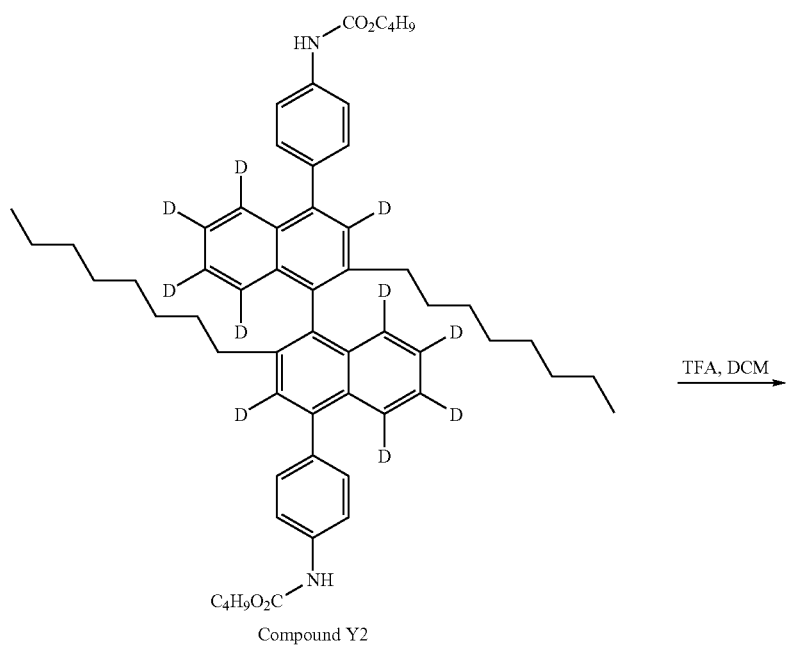

Compound Y2

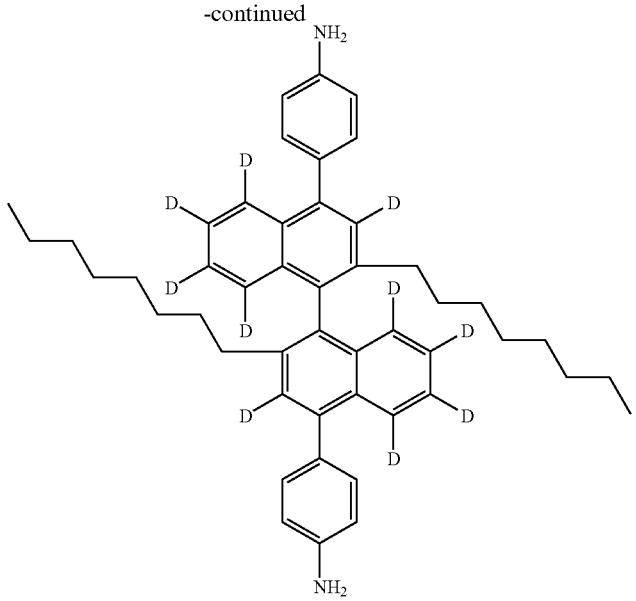

Compound Y3

Under nitrogen, a 100 mL round-bottomed flask was charged with compound Y2 (2.100 g, 2.410 mmol) and dichloromethane (30 mL). It was allowed to stir for 5 minutes and then trifluoroacetic acid (1.793 mL) was added and the reaction was left to stir overnight. Once the reaction was complete, it was quenched using saturated sodium carbonate solution. The water was removed and washed with CH2Cl2 and the combined organic layer was evaporated to dryness. The residue dissolved in diethyl ether and the product was washed with sodium carbonate, brine and water and dried using magnesium sulphate. Compound Y3 was purified using chromatography to yield 1.037 g.

Figure 2:
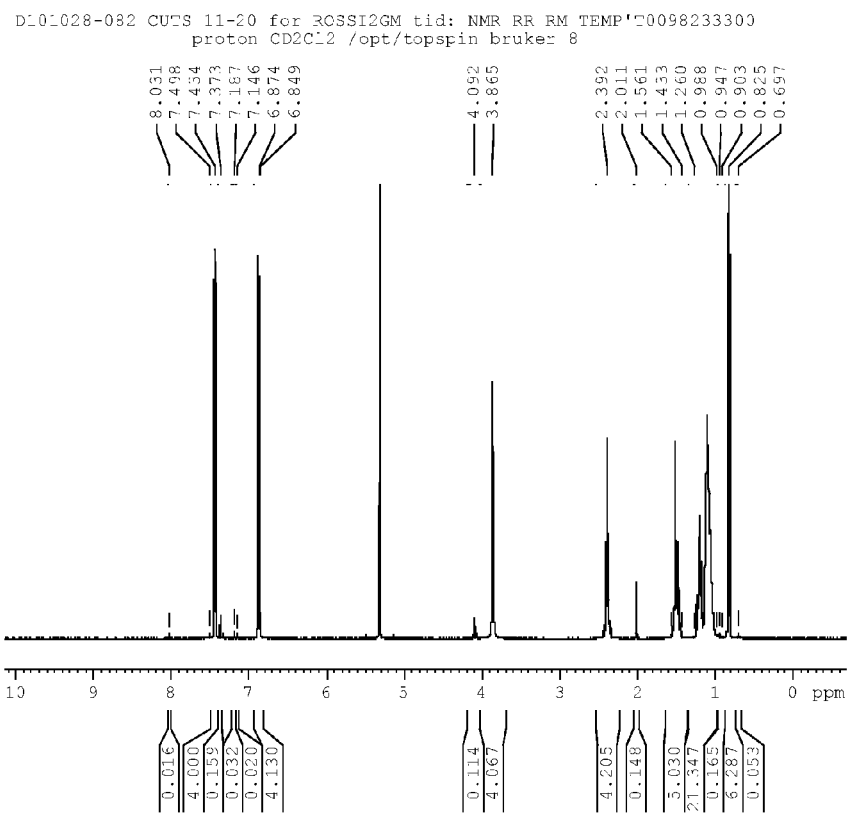
FIG. 2 includes the $^1$H NMR spectrum of a deuterated intermediate compound.

The structure of the compound was confirmed by $^1$H NMR, as shown in FIG. 2.

Synthesis of Intermediate Compound Y4:

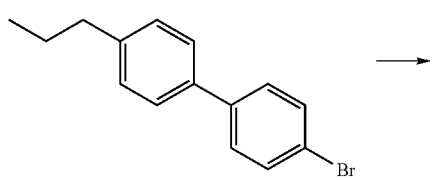

-continued

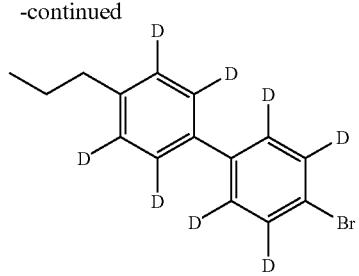

Compound Y4

A solution of 4-bromo-4'-propylbiphenyl (5.10 g, 18.53 mmol) in C6D6 (20 mL) was purged with nitrogen for 30 min. A 1.0 M solution of ethyl aluminum dichloride solution in hexanes (4.0 mL, 4.0 mmol) was added dropwise via syringe and the reaction mixture was heated at reflux for 1.75 h under nitrogen atmosphere. After cooling to room temperature under nitrogen atmosphere, deuterium oxide (20 mL) is added, the mixture is shaken, and the layers are separated. The aqueous layer is extracted with benzene (3×10 mL) and the combined organic phase is dried over magnesium sulfate, filtered and concentrated by rotary evaporation. The product thus obtained was resubjected to the above reaction conditions two more times. After the third treatment the crude product was recrystallized from ethanol (20 mL) to afford compound Y4 (1.01 g) as a white solid. Mp 110.1-111.6° C. Purity (UPLC): 100%. The $^1$H NMR spectrum of Y4 was consistent with an average of 7.64 of the 8 aromatic protons replaced by deuterium.

Synthesis of Intermediate Compound Y5:

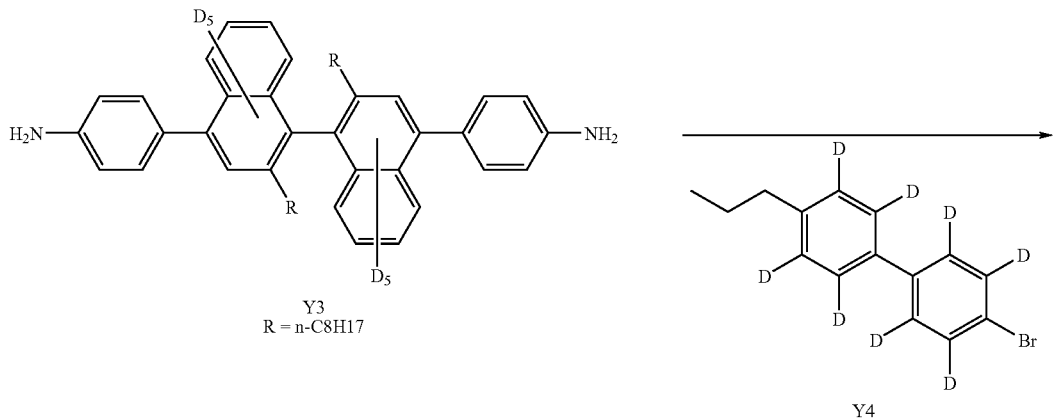

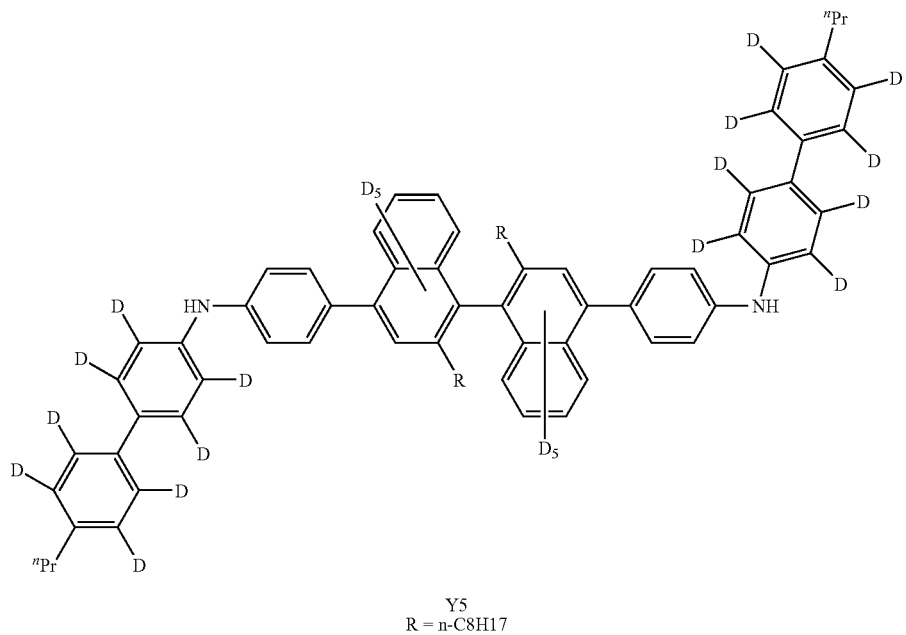

Under an atmosphere of nitrogen, compound Y3 (1.04 g, 1.55 mmol), Y4 (0.80 g, 2.82 mmol), tris(dibenzylideneacetone)dipalladium(0) (81 mg, 0.09 mmol), tri-t-butylphosphine (42 mg, 0.21 mol %) and toluene (25 mL) were combined. Sodium t-butoxide (0.52 g, 5.41 mmol) was added and the reaction was stirred at room temperature for 40 h. Tris (dibenzylideneacetone)dipalladium(0) (50 mg, 0.05 mmol), tri-t-butylphosphine (30 mg, 0.15 mmol) and Y4 (196 mg, 0.69 mmol) were then added and the reaction mixture was warmed to 50° C. After another 72 h, the reaction mixture was filtered through a pad of Celite, rinsing with CH2Cl2 (50 mL). The filtrate was concentrated on a rotary evaporator and dried under vacuum. The product was purified by medium pressure liquid chromatography on silica gel (0-40% methylene chloride gradient in hexanes) to give 0.99 g (59% yield) of a white solid. NMR analysis confirmed the structure of Intermediate Compound Y5 as a mixture of 4,4'- and 4,5'-regioisomers. Purity (UPLC): 99.3%.

Synthesis of Intermediate Compound Y6:

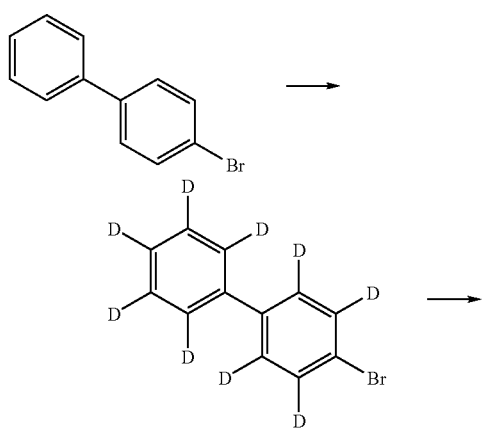

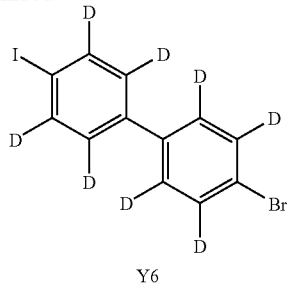

Y6

Step 1: Preparation of Deuterated 4-bromobiphenyl.

A solution of 4-bromobiphenyl (4.66 g, 20.0 mmol) in C6D6 (20 mL) was purged with nitrogen for 30 min. A 1.0 M solution of ethyl aluminum dichloride solution in hexanes (4.0 mL, 4.0 mmol) was added dropwise via syringe and the reaction mixture was heated at reflux for 50 min under nitrogen atmosphere. After cooling to room temperature under nitrogen atmosphere, deuterium oxide (20 mL) is added, the mixture is shaken, and the layers are separated. The organic phase is dried over magnesium sulfate, filtered and concentrated by rotary evaporation. The product thus obtained was resubjected to the above reaction conditions four more times. After the fifth treatment the crude product was recrystallized from ethanol (20 mL) to afford the title compound of Step 1 (2.26 g) as a white solid. Mp 92.8-94.1° C. Purity (UPLC): 98.14%. The mass spectrum indicated that 6-9 deuterium atoms had been incorporated.

Step 2: Preparation of Y6:

The product of Step 1 (2.26 g, 9.36 mmol) and iodic acid (687 mg) were dissolved in acetic acid (40 mL). Iodine chips (1.56 g) were added, followed by concentrated sulfuric acid (1.0 mL) and water (2.0 mL) and the reaction mixture was heated to reflux for 210 min. After cooling to room temperature, the precipitate was collected by filtration and washed with water, then methanol (20 mL each). The crude product was crystallized from EtOH/EtOAc (1/1) to afford Y6 (1.31 g) as a white solid. Mp 179.0-181.3° C. Purity (UPLC): 100%. The mass spectrum indicated that 6-7 deuterium atoms on average had been incorporated.

Synthesis of Intermediate Compound Y7:

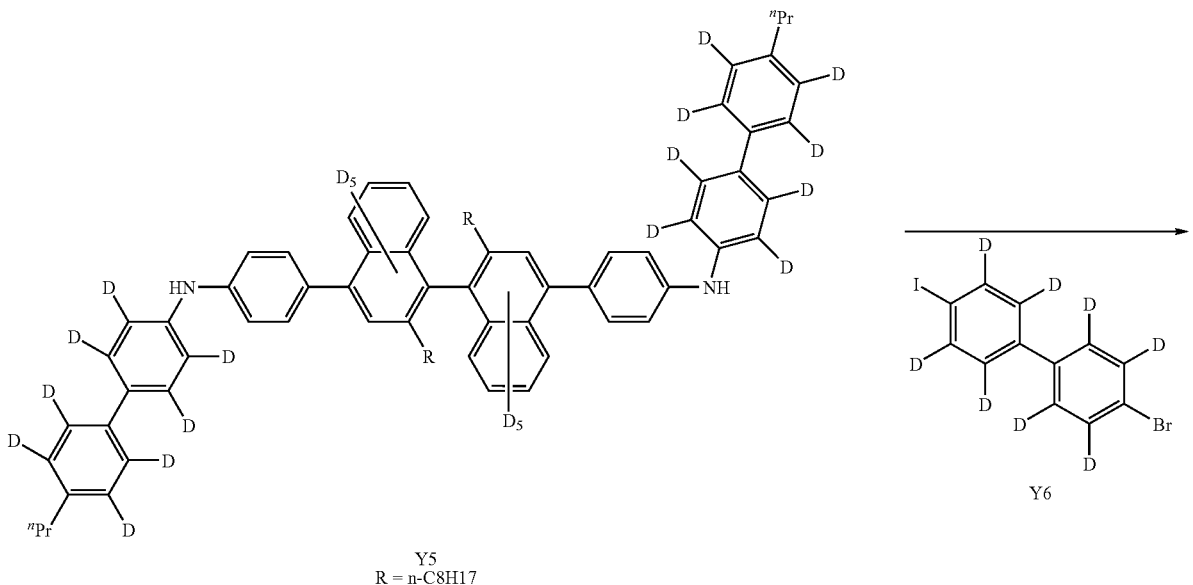

Y5
R = n-C8H17

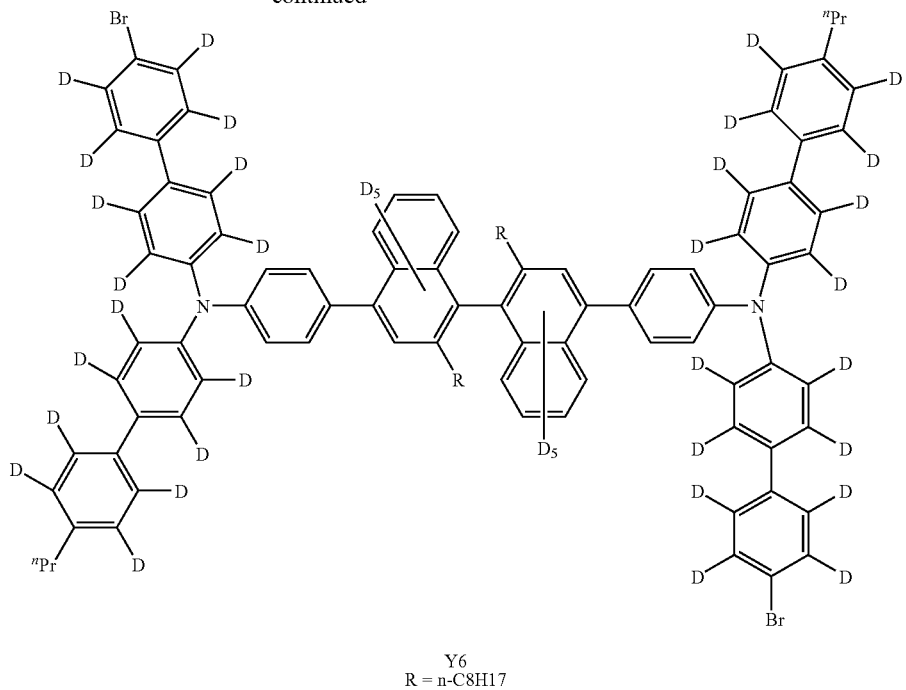

Y6
R = n-C8H17

In a nitrogen purged glovebox, a 3-neck round bottom flask equipped with a magnetic stirrer, thermometer and reflux condenser topped with a gas inlet adaptor in the closed position was charged with Y5 (986 mg, 0.92 mmol), Y6 (1.30 g, 3.55 mmol), tris(dibenzylideneacetone)dipalladium(0) (124 mg, 14.8 mol %), bis(diphenylphosphinoferrocene) (151 mg, 29.6 mol %) and toluene (20 mL) through the open neck. Sodium t-butoxide (0.30 g, 3.12 mmol) was added, the open neck was capped and the reaction vessel was removed from the glovebox. A nitrogen bubbler hose was fitted to the gas inlet adaptor and the stopcock was turned to the open position under a slight positive pressure of nitrogen. The reaction was heated at reflux. After 21 h, the reaction was judged complete by UPLC analysis of an aliquot and the reaction was cooled to room temperature. The reaction mixture was filtered through a pad of Celite, rinsing with CH2Cl2. The filtrate was concentrated by rotary evaporation. The crude product was dried under high vacuum and purified by medium pressure liquid chromatography on silica gel (0-40% methylene chloride gradient in hexanes) to give 1.21 g of a white solid that was triturated with boiling methanol for 2 h to afford 0.975 g of Y7. $^1$H NMR analysis confirmed the structure of Intermediate Compound Y7 as a mixture of 4,4'- and 4,5'-regioisomers and indicated that an average of 14 aromatic protons remained. This was corroborated by a parent ion (m/z 1550.3) in the mass spectrum confirming that 36 out of 50 aromatic hydrogens were replaced by deuterium. Purity (UPLC): >99%.
Synthesis of Compound H3:

The polymerization of intermediate compound Y7 was performed as described for comparative A. The polymer was obtained as a white solid in 68% yield (0.285 g). The molecular weight of the polymer was determined by GPC (THF mobile phase, polystyrene standards): $M_w$=325,740; $M_n$=139,748; $M_w/M_n$=2.33.

Example 2

This example illustrates the preparation of a deuterated electroactive compound, Compound P, where $\Sigma(x)$=18.
Synthesis of Compound 2

-continued

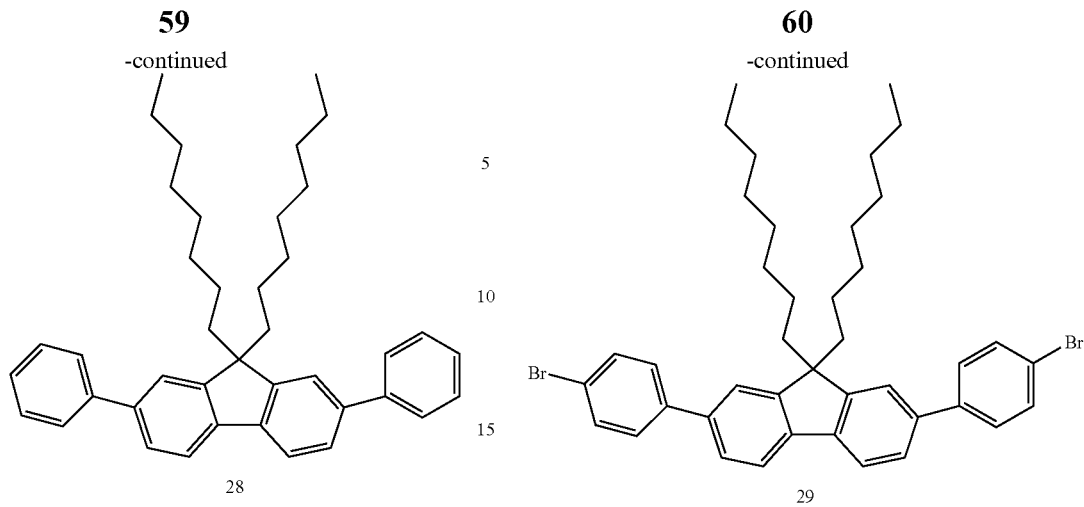

28

29

Under an atmosphere of nitrogen, a 250 mL round bottom was charged with 9,9-dioctyl-2,7-dibromofluorene (25.0 g, 45.58 mmol), phenylboronic acid (12.23 g, 100.28 mmol), Pd$_2$(dba)$_3$ (0.42 g, 0.46 mmol), P$^t$Bu$_3$ (0.22 g, 1.09 mmol) and 100 mL toluene. The reaction mixture stirred for five minutes after which KF (8.74 g, 150.43 mmol) was added in two portions and the resulting solution was stirred at room temperature overnight. The mixture was diluted with 500 mL THF and filtered through a plug of silica and celite and the volatiles were removed from the filtrate under reduced pressure. The yellow oil was purified by flash column chromatography on silica gel using hexanes as eluent. The product was obtained as a white solid in 80.0% (19.8 g). Analysis by NMR indicated the material to be compound 2 having structure given above.

Synthesis of Compound 3

A 250 mL three-necked-round-bottom-flask, equipped with a condenser and dripping funnel was flushed with N$_2$ for 30 minutes. 9,9-dioctyl-2,7-diphenylfluorene (19.8 g, 36.48 mmol) was added and dissolved in 100 mL dichloromethane. The clear solution was cooled to −10° C. and a solution of bromine (12.24 g, 76.60 mmol) in 20 mL dichloromethane was added dropwise. The mixture was stirred for one hour at 0° C. and then allowed to warm to room temperature and stirred overnight. 100 mL of an aqueous 10% Na$_2$S$_2$O$_3$ solution was added and the reaction mixture was stirred for one hour. The organic layer was extracted and the water layer was washed three times with 100 mL dichloromethane. The combined organic layers were dried with Na$_2$SO$_4$ filtered and concentrated to dryness. Addition of acetone to the resulting oil gave a white precipitated. Upon filtration and drying a white powder was obtained (13.3 g, 52.2%). Analysis by NMR indicated the material to be compound 3 having structure given above.

Synthesis of Compound 4

(10)

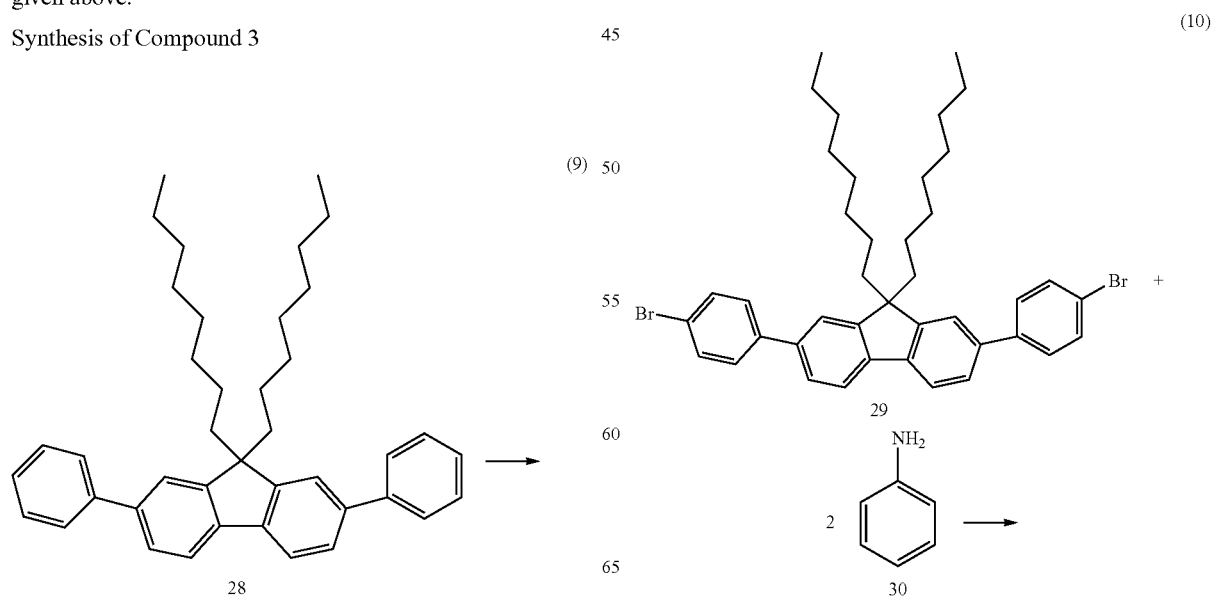

(9)

28

29

2

30

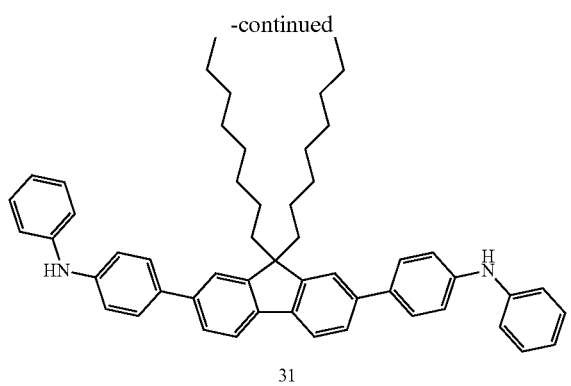

31

Under an atmosphere of nitrogen, a 250 mL round bottom was charged with 3 (13.1 g, 18.70 mmol), aniline (3.66 g, 39.27 mmol), Pd₂(dba)₃ (0.34 g, 0.37 mmol), P$^t$Bu₃ (0.15 g, 0.75 mmol) and 100 mL toluene. The reaction mixture stirred for 10 min after which NaO$^t$Bu (3.68 g, 38.33 mmol) was added and the reaction mixture was stirred at room temperature for one day. The resulting reaction mixture was diluted with 3 L toluene and filtered through a plug of silica and celite. Upon evaporation of volatiles, the dark brown oil obtained was purified by flash column chromatography on silica gel using a mixture of 1:10 ethyl acetate:hexanes as eluent. The product was obtained as a pale yellow powder in 50.2% (6.8 g). Analysis by NMR indicated the material to be compound 4 having structure given above.

Synthesis of Compound 5

(11)

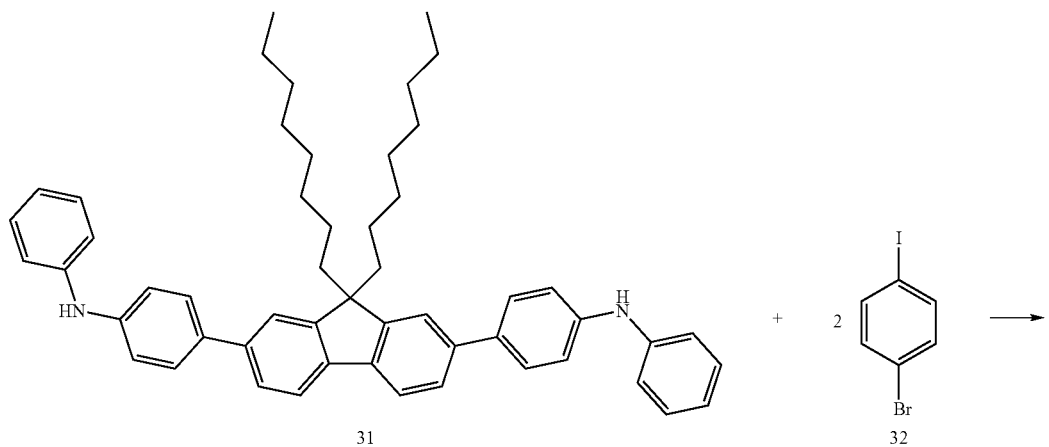

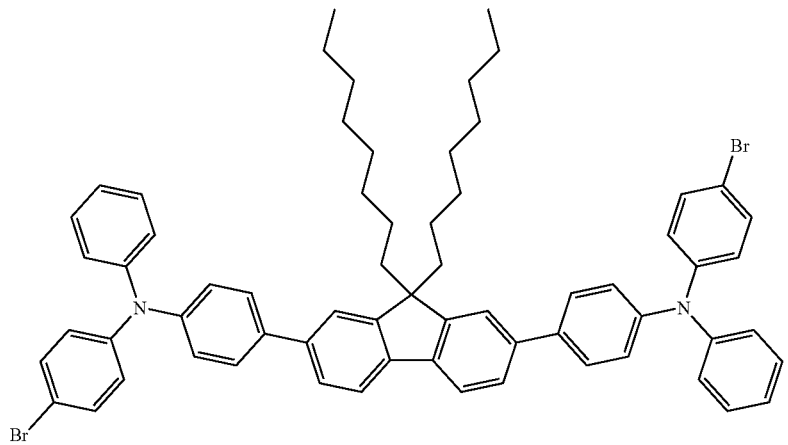

33

In a 250 mL three-necked-round-bottom-flask equipped with condenser, 4 (4.00 g, 5.52 mmol), 1-bromo-4-iodobenzene (4.68 g, 16.55 mmol), Pd$_2$(dba)$_3$ (0.30 g, 0.33 mmol) and DPPF (0.37 g, 0.66 mmol) were combined with 80 mL toluene. The resultant mixture was stirred for 10 min. NaO$^t$Bu (1.17 g, 12.14 mmol) was added and the mixture was heated to 80° C. for four days. The resulting reaction mixture was diluted with 1 L toluene and 1 L THF filtered through a plug of silica and celite to remove the insoluble salts. Upon evaporation of volatiles, the resulting brown oil was purified by flash column chromatography on silica gel using a mixture of 1:10 dichloromethane:hexanes as eluent. After drying a yellow powder was obtained (4.8 g, 84.8%). Analysis by NMR indicated the material to be compound 5 having structure given above.

Synthesis of Compound 6

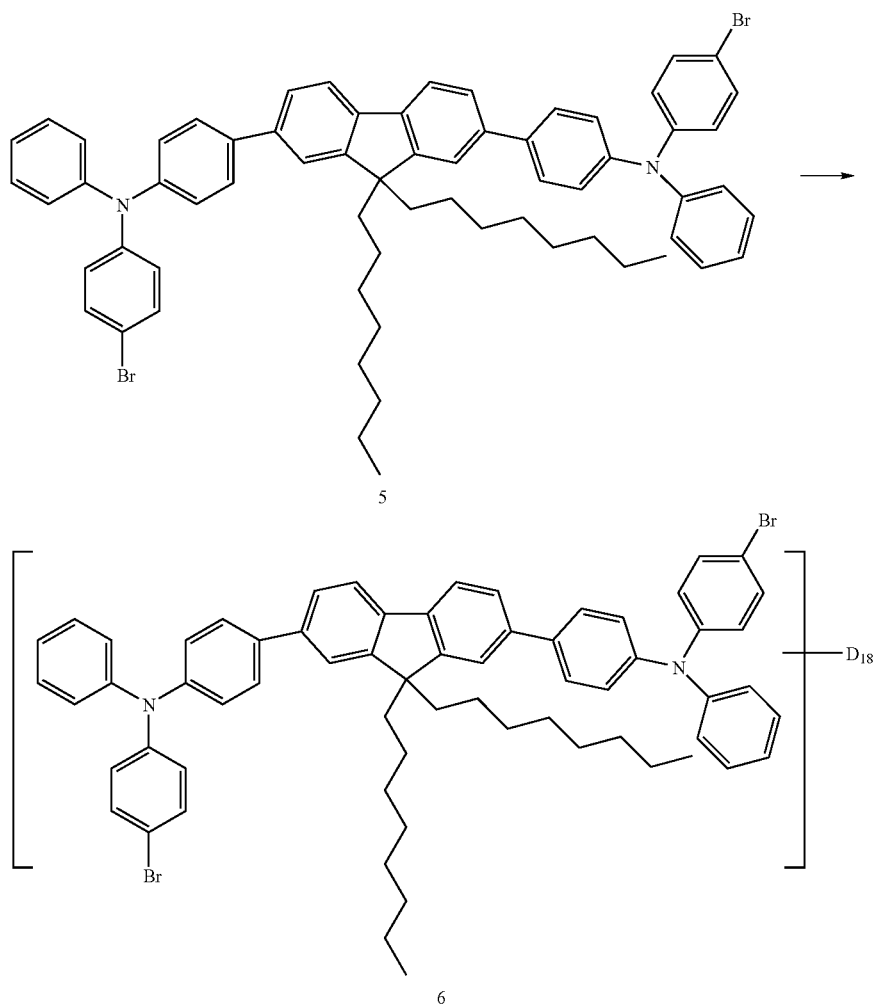

Under an atmosphere of nitrogen 1 g of compound 5 was dissolved in C$_6$D$_6$ (20 mL) to which CF$_3$OSO$_2$D (1.4 mL) was added dropwise. The reaction mixture was allowed to stir at room temperate overnight and then it was quenched with satd. Na$_2$CO$_3$/D$_2$O. The organic layer was isolated and dried over MgSO$_4$. The product was purified using silica chromatography (20% CH2Cl2:hexane) to yield 0.688 g of material. The MS spectrum of the isolated material confirmed the structure with 18 aromatic D.

Polymerization of Compound 6:

All operations were carried out in a nitrogen purged glovebox unless otherwise noted. Compound 6 (0.652 g, 0.50 mmol) was added to a scintillation vial and dissolved in 16 mL toluene. A clean, dry 50 mL Schlenk tube was charged with bis(1,5-cyclooctadiene)nickel(0) (0.344 g, 1.252 mmol). 2,2'-Dipyridyl (0.195 g, 1.252 mmol) and 1,5-cyclooctadiene (0.135 g, 1.252 mmol) were weighed into a scintillation vial and dissolved in 3.79 g N,N'-dimethylformamide. The solution was added to the Schlenk tube. The Schlenk tube was inserted into an aluminum block and the block was heated and stirred on a hotplate/stirrer at a setpoint that resulted in an internal temperature of 60° C. The catalyst system was held at 60° C. for 45 minutes and then raised to 65° C. The monomer solution in toluene was added to the Schlenk tube and the tube was sealed. The polymerization mixture was stirred at 65° C. for one while adjusting viscosity by adding toluene (8 mL). The reaction mixture was allowed to cool to room temperature and 20 mL of conc. HCl was added. The mixture was allowed to stir for 45 minutes. The polymer was collected by vacuum filtration and washed with additional methanol and dried under high vacuum. The polymer was purified by successive precipitations from toluene into acetone and MeOH, A white, fibrous polymer (0.437 g, 79% yield) was obtained. The molecular weight of the polymer was determined by GPC (THF mobile phase, polystyrene standards): $M_w$=1,696,019; $M_n$=873,259. NMR analysis confirmed the structure to be the polymer, Compound P.

DEVICE EXAMPLES

The following materials were used:
HIJ-1: made from which is an aqueous dispersion of an electrically conductive polymer and a polymeric fluorinated sulfonic acid. Such materials have been described in, for example, published U.S. patent applications US 2004/0102577, US 2004/0127637, and US 2005/0205860.

Host 1:

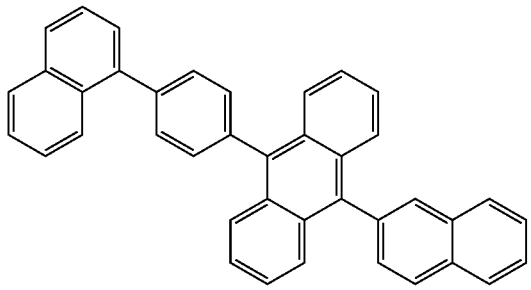

Emitter 1:

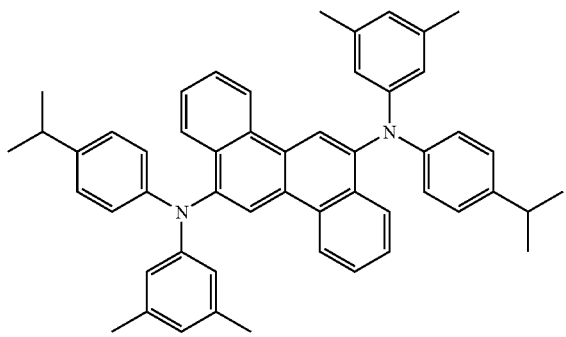

Device Example 1

This example demonstrates the fabrication and performance of a device using a deuterated material of the invention in a hole transport layer.
The device had the following structure on a glass substrate:
anode=Indium Tin Oxide (ITO): 50 nm
hole injection layer=HIJ-1 (50 nm)
hole transport layer=Compound H3 (20 nm)
electroactive layer=6:1 Host 1:Emitter 1 (40 nm)
electron transport layer=a metal quinolate derivative (10 nm)
cathode=CsF/Al (1.0/100 nm)
Four devices, designated as Exs. 1-1 through 1-4, were made and tested as described below.

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 50 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent. After cooling, the substrates were then spin-coated with a solution of the hole transport material, and then heated to remove solvent. After cooling, the substrates were spin-coated with the emissive layer solution, and heated to remove solvent. The substrates were masked and placed in a vacuum chamber. The electron transport layer was deposited by thermal evaporation, followed by a layer of CsF. Masks were then changed in vacuo and a layer of Al was deposited by thermal evaporation. The chamber was vented, and the devices were encapsulated using a glass lid, desiccant, and UV curable epoxy.

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is 1 m/W. The results are given in Table 1, below.

Comparative Device Example

A comparative device was prepared as described above in Device Example 1, except that the hole transport layer was Comparative A. Two devices, designated as Comp. A-1 and Comp. A-2, were made and tested as described above. The results are given in Table 1 below.

TABLE 1

| | | | | | | Device Results | | | |
|---|---|---|---|---|---|---|---|---|---|
| Example | CIE (x, y) | V | C.E. (cd/A) | E.Q.E. (%) | P.E. (lm/W) | Test current density (mA/cm2) | Test lum. (nits) | Raw T50 (h) | T50 @ 1000 nits (h) |
| Comp. A-1 | 0.138, 0.107 | 3.8 | 7.3 | 7.9 | 6.1 | 128 | 7515 | 214 | 6601 |
| Comp. A-2 | 0.138, 0.107 | 3.8 | 7.1 | 7.6 | 5.9 | 122 | 7175 | 214 | 6102 |
| Ex. 1-1 | 0.138, 0.107 | 3.7 | 7.2 | 7.7 | 6.0 | 129 | 7607 | 241 | 7589 |

TABLE 1-continued

Device Results

| Example | CIE (x, y) | V | C.E. (cd/A) | E.Q.E. (%) | P.E. (lm/W) | Test current density (mA/cm2) | Test lum. (nits) | Raw T50 (h) | T50 @ 1000 nits (h) |
|---|---|---|---|---|---|---|---|---|---|
| Ex. 1-2 | 0.138, 0.107 | 3.8 | 7.3 | 7.9 | 6.1 | 127 | 7631 | 258 | 8168 |
| Ex. 1-3 | 0.138, 0.107 | 3.7 | 7.2 | 7.8 | 6.1 | 130 | 7583 | 240 | 7517 |
| Ex. 1-4 | 0.139, 0.106 | 3.8 | 7.0 | 7.5 | 5.8 | 116 | 6595 | 297 | 7338 |

All data @ 1000 nits, C.E. = current efficiency; CIE[x] and CIE[y] refer to the x and y color coordinates according to the C.I.E. chromaticity scale (Commission Internationale de L'Eclairage, 1931); E.Q.E. = quantum efficiency; P.E. = power efficiency; "Test" = lifetime test; T50 = time to reach 50% of initial luminance; T50 @1000 nits is projected lifetime using an acceleration factor of 1.7; V = voltage, in volts.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner, slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. A compound having Formula I, Formula II, or Formula III:

(I)

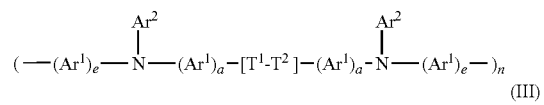

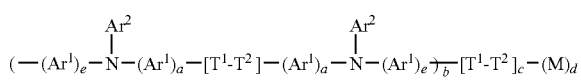

wherein:

Ar$^1$ is the same or different at each occurrence and is selected from the group consisting of phenylene, substituted phenylene, naphthylene, and substituted naphthylene;

Ar$^2$ is the same or different at each occurrence and is an aryl group;

M is the same or different at each occurrence and is a conjugated moiety;

T$^1$ and T$^2$ are independently the same or different at each occurrence and are conjugated moieties;

a is the same or different at each occurrence and is an integer from 1 to 6;

b, c, and d are mole fractions such that b+c+d=1.0, with the proviso that c is not zero, and at least one of b and d is not zero, and when b is zero, M comprises at least two triarylamine units;

e is the same or different at each occurrence and is an integer from 1 to 6; and n is an integer greater than 1 wherein the compound is at least 10% deuterated.

2. The compound of claim 1, having at least one substituent group on an aryl ring, wherein deuteration is on the substituent group on an aryl ring.

3. The compound of claim 1, wherein at least one of Ar$^1$ and Ar$^2$ is a deuterated aryl group.

4. The compound of claim 3, wherein Ar$^1$ and Ar$^2$ are at least 20% deuterated.

5. The compound of claim 1, having at least one substituent group on an aryl ring, wherein deuteration is present on both at least one substituent group and at least one aryl ring.

6. The compound of claim 1, wherein deuteration is present on [T$^1$-T$^2$].

7. The compound of claim 6, wherein [T$^1$-T$^2$] is at least 20% deuterated.

8. The compound of claim 7, wherein Ar$^1$ and Ar$^2$ are at least 20% deuterated.

9. The compound of claim 6, wherein at least one of Ar$^1$ and Ar$^2$ is a deuterated aryl group.

10. The compound of claim 1, wherein [$T^1$-$T^2$] is selected from the group consisting of:

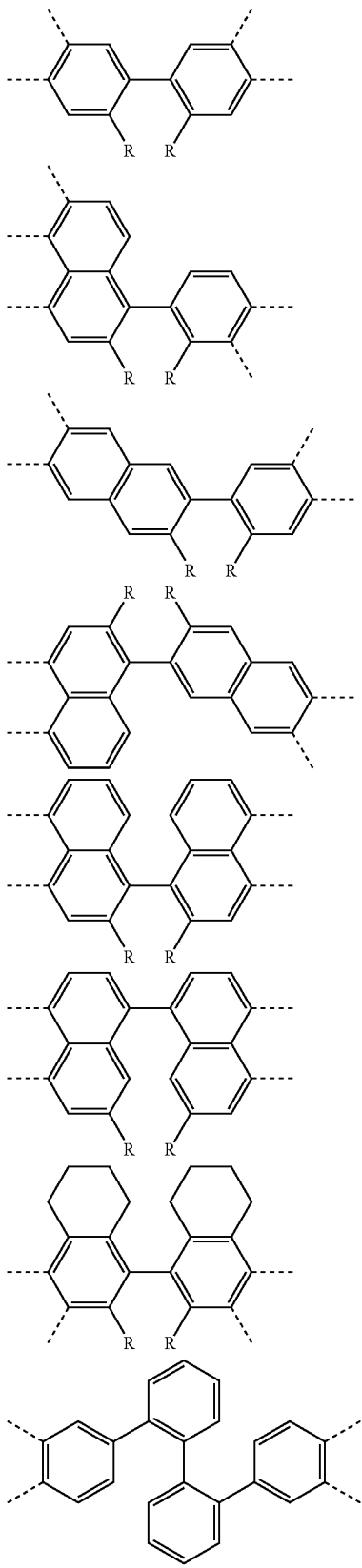

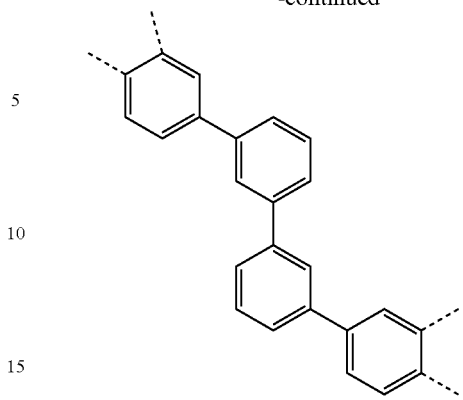

and deuterated analogs thereof,
where:
R is the same or different and is selected from the group consisting of alkyl, aryl, alkoxy, aryloxy, fluoroalkyl, fluoroaryl, fluoroaryloxy fluoroalkyloxy, oxyalkyl, and alkenyl groups.

11. The compound of claim 10, wherein R is selected from the group consisting of C1-10 alkyl and C1-10 alkoxy.

12. The compound of claim 1, wherein a is 1-3.

13. The compound of claim 12, wherein M is selected from the group consisting of triarylamine units, an aromatic unit having a crosslinkable substituent, and deuterated analogs thereof.

14. The compound of claim 1, wherein $Ar^2$ has Formula a

Formula a

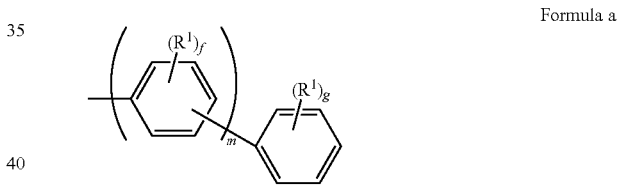

where:
$R^1$ is the same or different at each occurrence and is selected from the group consisting of D, alkyl, alkoxy, siloxane and, silyl; or adjacent $R^1$ groups may be joined to form an aromatic ring;
f is the same or different at each occurrence and is an integer from 0-4;
g is an integer from 0-5; and
m is an integer from 1 to 5.

15. The compound of claim 1, wherein $Ar^2$ is selected from the group consisting phenyl, p-biphenyl, p-terphenyl, naphthyl, phenylnaphthyl, naphthylphenyl, and deuterated analogs thereof.

16. The compound of claim 1, wherein $Ar^2$ has a substituent comprising a crosslinking group.

17. The compound of claim 1 having Formula III, wherein c is at least 0.4.

18. The compound of claim 1, wherein [$T^1$-$T^2$] is a substituted biphenylene group, or deuterated analog thereof.

19. The compound of claim 1, wherein [$T^1$-$T^2$] is a binaphthylene group, or deuterated analog thereof.

20. An organic electronic device comprising a first electrical contact layer, a second electrical contact layer and an active layer therebetween, wherein the active layer comprises a compound having Formula I, Formula II, or Formula III:

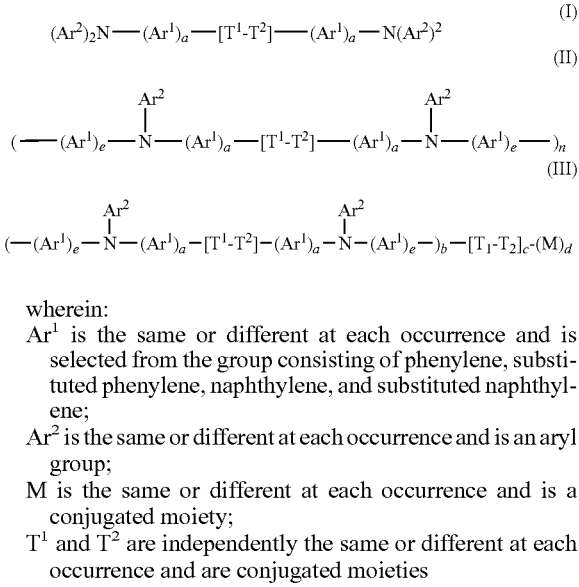

wherein:
Ar$^1$ is the same or different at each occurrence and is selected from the group consisting of phenylene, substituted phenylene, naphthylene, and substituted naphthylene;
Ar$^2$ is the same or different at each occurrence and is an aryl group;
M is the same or different at each occurrence and is a conjugated moiety;
T$^1$ and T$^2$ are independently the same or different at each occurrence and are conjugated moieties a is the same or different at each occurrence and is an integer from 1 to 6;
b, c, and d are mole fractions such that b+c+d=1.0, with the proviso that c is not zero, and at least one of b and d is not zero, and when b is zero, M comprises at least two triarylamine units;
e is the same or different at each occurrence and is an integer from 1 to 6; and
n is an integer greater than 1
wherein the compound is at least 10% deuterated.

21. The device of claim 20, wherein the active layer is a hole transport layer.

22. The device of claim 20, wherein the hole transport layer consists essentially of the compound having Formula I, Formula II, or Formula III.

23. The device of claim 20, wherein the active layer is an electroluminescent layer.

24. The device of claim 20, wherein the active layer consists essentially of one or more electroluminescent materials and a compound having Formula I, Formula II, or Formula III.

* * * * *